(12) United States Patent
Sengun et al.

(10) Patent No.: US 9,974,643 B2
(45) Date of Patent: May 22, 2018

(54) IMPLANT HAVING ADJUSTABLE FILAMENT COILS

(71) Applicant: Medos International Sàrl, Le Locle (CH)

(72) Inventors: Mehmet Ziya Sengun, Canton, MA (US); Hugh S. West, Murray, UT (US); Meghan A. Pasquali, Providence, RI (US); David B. Spenciner, North Attleboro, MA (US); William Reiser, West Jordan, UT (US); Jeff Parrish, Kaysville, UT (US)

(73) Assignee: MEDOS INTERNATIONAL SÀRL, Le Locle (CH)

( * ) Notice: Subject to any disclaimer, the term of this patent is extended or adjusted under 35 U.S.C. 154(b) by 743 days.

(21) Appl. No.: 13/793,514

(22) Filed: Mar. 11, 2013

(65) Prior Publication Data
US 2014/0257346 A1 Sep. 11, 2014

(51) Int. Cl.
*A61F 2/08* (2006.01)
*A61B 17/04* (2006.01)
*A61B 17/06* (2006.01)

(52) U.S. Cl.
CPC ........ *A61F 2/0811* (2013.01); *A61B 17/0401* (2013.01); *A61B 2017/0404* (2013.01);
(Continued)

(58) Field of Classification Search
CPC .... A61B 2017/0475; A61B 2017/0477; A61B 2017/0458; A61B 17/0401;
(Continued)

(56) References Cited

U.S. PATENT DOCUMENTS 1,426,537 A 8/1922 Bauer
2,151,664 A 3/1939 Erwin
(Continued)

FOREIGN PATENT DOCUMENTS

FR 2743294 A1 7/1997
WO 92/006648 A1 4/1992
(Continued)

OTHER PUBLICATIONS

Extended European Search Report for Appliciation No. 14158607.3, dated Aug. 21, 2014 (6 pages).
(Continued)

*Primary Examiner* — Eric Rosen
*Assistant Examiner* — Chima Igboko

(57) ABSTRACT

A device having one or more adjustable loops or coils associated with an implant body for use in soft tissue reconstructions is provided. One exemplary embodiment of a device includes a body and a suture filament, with the filament being used to form a self-locking sliding knot disposed on a top side of the body and a plurality of adjustable coils that are substantially disposed on the body's bottom side. Terminal ends of the filament located above the body's top side can be passed through an opening of a Lark's Head knot from opposite sides, thus forming a self-locking sliding knot, and then the terminal ends can be tensioned to adjust a circumference of the coils. Changing a coil's circumference changes a location of a ligament graft disposed on the coil. Other configurations of devices and systems, as well as methods for performing ACL repairs, are also provided.

20 Claims, 15 Drawing Sheets

(52) U.S. Cl.
CPC ............... *A61B 2017/0458* (2013.01); *A61B 2017/0475* (2013.01); *A61B 2017/06185* (2013.01); *A61F 2002/0829* (2013.01); *A61F 2002/0852* (2013.01); *A61F 2002/0882* (2013.01)

(58) Field of Classification Search
CPC .... A61B 2017/0403; A61B 2017/0404; A61B 2017/0406; A61B 2017/0408; A61B 2017/0409; A61B 2017/0411; A61B 2017/0417; A61B 2017/0414; A61B 2017/0419; A61B 2017/0448; A61B 2017/0446; A61B 2017/0459; A61B 2002/0823; A61B 2002/0817; A61B 2/0811; A61B 2/0805; A61B 2002/0829; A61B 2002/0841; A61B 2002/0847; A61B 2002/0852; A61B 2002/0858; A61B 2002/0864; A61B 2002/087; A61B 2002/0876; A61B 2002/0882; A61B 2002/0888
USPC ........................................................ 606/232
See application file for complete search history.

(56) References Cited

U.S. PATENT DOCUMENTS

| | | |
|---|---|---|
| 2,600,395 A | 6/1952 | Domoj et al. |
| 4,093,292 A | 6/1978 | Marcet et al. |
| 4,105,349 A | 8/1978 | Kupperman et al. |
| 4,133,604 A | 1/1979 | Fuller |
| 4,186,921 A | 2/1980 | Fox |
| 4,233,917 A | 11/1980 | Carnaby |
| 4,255,836 A | 3/1981 | Dunahoo |
| 4,257,309 A | 3/1981 | Dunahoo |
| 4,319,428 A | 3/1982 | Fox |
| 4,469,101 A | 9/1984 | Coleman et al. |
| 4,510,934 A | 4/1985 | Batra |
| 4,527,564 A | 7/1985 | Eguchi et al. |
| 4,582,165 A | 4/1986 | Latini |
| 4,604,821 A | 8/1986 | Moser |
| 4,705,040 A | 11/1987 | Mueller et al. |
| 4,723,634 A | 2/1988 | Fisk |
| 4,750,492 A | 6/1988 | Jacobs |
| 4,773,910 A | 9/1988 | Chen et al. |
| 4,781,191 A | 11/1988 | Thompson |
| 4,823,794 A | 4/1989 | Pierce |
| 4,890,363 A | 1/1990 | Cross |
| 4,910,834 A | 3/1990 | Minkler |
| 4,946,377 A | 8/1990 | Kovach |
| 4,962,929 A | 10/1990 | Melton, Jr. |
| 4,971,075 A | 11/1990 | Lee |
| 4,997,433 A | 3/1991 | Goble et al. |
| 5,062,344 A | 11/1991 | Gerker |
| 5,074,291 A | 12/1991 | Carter |
| 5,083,875 A | 1/1992 | Cedrone |
| 5,139,520 A | 8/1992 | Rosenberg |
| 5,168,605 A | 12/1992 | Bartlett |
| 5,178,629 A | 1/1993 | Kammerer |
| 5,217,092 A | 6/1993 | Potter |
| 5,219,359 A | 6/1993 | McQuilkin et al. |
| 5,269,783 A | 12/1993 | Sander |
| 5,306,290 A | 4/1994 | Martins et al. |
| 5,306,301 A * | 4/1994 | Graf .................. A61B 17/0401 606/151 |
| 5,374,268 A | 12/1994 | Sander |
| 5,374,269 A | 12/1994 | Rosenberg |
| 5,451,203 A | 9/1995 | Lamb |
| 5,505,735 A | 4/1996 | Li |
| 5,531,759 A | 7/1996 | Kensey et al. |
| 5,540,703 A | 7/1996 | Barker, Jr. et al. |
| 5,573,286 A * | 11/1996 | Rogozinski ............ A61B 17/82 289/1.2 |
| 5,575,819 A | 11/1996 | Amis |
| 5,628,756 A | 5/1997 | Barker |
| 5,645,588 A | 7/1997 | Graf et al. |
| 5,649,541 A | 7/1997 | Stuckey |
| 5,667,528 A | 9/1997 | Colligan |
| 5,693,060 A | 12/1997 | Martin |
| 5,707,373 A | 1/1998 | Sevrain et al. |
| 5,769,894 A | 6/1998 | Ferragamo |
| 5,778,904 A | 7/1998 | Elsner |
| 5,921,986 A | 7/1999 | Bonutti |
| 5,928,267 A | 7/1999 | Bonutti et al. |
| 5,964,764 A | 10/1999 | West, Jr. et al. |
| 5,984,926 A | 11/1999 | Jones |
| 5,989,252 A | 11/1999 | Fumex |
| 5,997,051 A | 12/1999 | Kissner et al. |
| 6,013,083 A | 1/2000 | Bennett |
| 6,030,007 A | 2/2000 | Bassily et al. |
| 6,045,551 A * | 4/2000 | Bonutti .............. A61B 17/0401 606/215 |
| 6,056,752 A | 5/2000 | Roger |
| 6,086,591 A | 7/2000 | Bojarski |
| 6,099,568 A | 8/2000 | Simonian |
| 6,110,207 A | 8/2000 | Eichhorn et al. |
| 6,117,160 A | 9/2000 | Bonutti |
| 6,143,029 A | 11/2000 | Rippstein |
| 6,193,754 B1 | 2/2001 | Seedhom |
| 6,203,572 B1 | 3/2001 | Johnson et al. |
| 6,206,886 B1 | 3/2001 | Bennett |
| 6,238,395 B1 | 5/2001 | Bonutti |
| 6,258,091 B1 | 7/2001 | Sevrain et al. |
| 6,293,961 B2 | 9/2001 | Schwartz et al. |
| 6,296,659 B1 | 10/2001 | Foerster |
| 6,306,159 B1 | 10/2001 | Schwartz |
| 6,319,271 B1 | 11/2001 | Schwartz et al. |
| 6,342,060 B1 | 1/2002 | Adams |
| 6,352,603 B1 | 3/2002 | Bryant |
| 6,418,576 B1 | 7/2002 | Starkweather |
| 6,440,134 B1 | 8/2002 | Zaccherotti et al. |
| 6,453,974 B1 | 9/2002 | Lai et al. |
| 6,503,267 B2 | 1/2003 | Bonutti et al. |
| 6,517,578 B2 | 2/2003 | Hein |
| 6,527,795 B1 | 3/2003 | Lizardi |
| 6,533,802 B2 | 3/2003 | Bojarski et al. |
| 6,558,389 B2 | 5/2003 | Clark et al. |
| 6,585,121 B1 | 7/2003 | Smeets et al. |
| 6,589,244 B1 | 7/2003 | Sevrain et al. |
| 6,592,609 B1 | 7/2003 | Bonutti |
| 6,599,319 B2 | 7/2003 | Knudsen et al. |
| 6,602,290 B2 | 8/2003 | Esnouf et al. |
| 6,619,703 B2 | 9/2003 | Dirks et al. |
| 6,638,279 B2 | 10/2003 | Bonutti |
| 6,699,286 B2 | 3/2004 | Sklar |
| 6,712,849 B2 | 3/2004 | Re |
| 6,761,722 B2 | 7/2004 | Cole et al. |
| 6,833,005 B1 | 12/2004 | Mantas et al. |
| 6,902,573 B2 | 6/2005 | Strobel et al. |
| 6,972,027 B2 | 12/2005 | Fallin et al. |
| 6,997,480 B2 | 2/2006 | Legrand |
| 6,997,940 B2 | 2/2006 | Bonutti |
| 7,033,380 B2 | 4/2006 | Schwartz et al. |
| 7,063,724 B2 | 6/2006 | Re et al. |
| 7,076,845 B2 | 7/2006 | Tylaska et al. |
| 7,097,654 B1 | 8/2006 | Freedland |
| 7,150,757 B2 | 12/2006 | Fallin et al. |
| 7,235,091 B2 | 6/2007 | Thornes |
| 7,285,124 B2 | 10/2007 | Foerster |
| 7,306,417 B2 | 12/2007 | Dorstewitz |
| 7,390,332 B2 | 6/2008 | Selvitelli et al. |
| 7,407,512 B2 | 8/2008 | Bojarski et al. |
| 7,442,210 B2 | 10/2008 | Segal et al. |
| 7,481,825 B2 | 1/2009 | Bonutti |
| 7,488,347 B1 | 2/2009 | Goble et al. |
| 7,500,983 B1 | 3/2009 | Kaiser et al. |
| 7,500,990 B2 | 3/2009 | Whelan |
| 7,520,898 B2 | 4/2009 | Re et al. |
| 7,530,990 B2 | 5/2009 | Perriello et al. |
| 7,566,339 B2 | 7/2009 | Fallin et al. |
| 7,572,275 B2 | 8/2009 | Fallin et al. |
| 7,594,923 B2 | 9/2009 | Fallin et al. |
| 7,601,165 B2 | 10/2009 | Stone |

(56) References Cited

U.S. PATENT DOCUMENTS

| | | |
|---|---|---|
| 7,632,311 B2 | 12/2009 | Seedhom et al. |
| 7,641,694 B1 | 1/2010 | Goble et al. |
| 7,645,282 B2 | 1/2010 | Huxel et al. |
| 7,658,751 B2 | 2/2010 | Stone et al. |
| 7,682,374 B2 | 3/2010 | Foerster et al. |
| 7,686,838 B2 | 3/2010 | Wolf et al. |
| 7,695,503 B1 | 4/2010 | Kaiser et al. |
| 7,703,372 B1 | 4/2010 | Shakespeare |
| 7,722,644 B2 | 5/2010 | Fallin et al. |
| 7,749,250 B2 | 7/2010 | Stone et al. |
| 7,776,039 B2 | 8/2010 | Bernstein et al. |
| 7,806,909 B2 | 10/2010 | Fallin et al. |
| 7,845,669 B2 | 12/2010 | Yeh et al. |
| 7,846,181 B2 | 12/2010 | Schwartz et al. |
| 7,857,830 B2 | 12/2010 | Stone et al. |
| 7,875,057 B2 | 1/2011 | Cook et al. |
| 7,875,058 B2 | 1/2011 | Holmes, Jr. |
| 7,887,551 B2 | 2/2011 | Bojarski et al. |
| 7,892,238 B2 | 2/2011 | DiPoto et al. |
| 7,892,256 B2 | 2/2011 | Grafton et al. |
| 7,901,431 B2 | 3/2011 | Shurnas |
| 7,905,903 B2 | 3/2011 | Stone et al. |
| 7,959,650 B2 | 6/2011 | Kaiser et al. |
| 8,012,171 B2 | 9/2011 | Schmieding |
| 8,088,130 B2 | 1/2012 | Kaiser et al. |
| 8,118,836 B2 | 2/2012 | Denham et al. |
| 8,127,652 B1 | 3/2012 | Hennings et al. |
| 8,128,658 B2 | 3/2012 | Kaiser et al. |
| 8,136,438 B2 | 3/2012 | Shakespeare |
| 8,137,382 B2 | 3/2012 | Denham et al. |
| 8,147,514 B2 | 4/2012 | Bonutti |
| 8,202,298 B2 | 6/2012 | Cook et al. |
| 8,221,455 B2 | 7/2012 | Shurnas et al. |
| 8,231,654 B2 | 7/2012 | Kaiser et al. |
| 8,231,674 B2 | 7/2012 | Albertorio et al. |
| 8,257,394 B2 | 9/2012 | Saadat et al. |
| 8,298,271 B2 | 10/2012 | Jacene et al. |
| 8,366,744 B2 | 2/2013 | Bojarski et al. |
| 8,388,655 B2 | 3/2013 | Fallin et al. |
| 8,398,678 B2 | 3/2013 | Baker et al. |
| 8,439,976 B2 | 5/2013 | Albertorio et al. |
| 8,460,379 B2 | 6/2013 | Albertorio et al. |
| 8,475,534 B2 | 7/2013 | Karnes et al. |
| 8,512,376 B2 | 8/2013 | Thornes |
| 8,523,943 B2 | 9/2013 | Hart |
| 8,535,313 B1 | 9/2013 | Masson |
| 8,591,578 B2 | 11/2013 | Albertorio et al. |
| 8,617,185 B2 | 12/2013 | Bonutti et al. |
| 8,628,573 B2 | 1/2014 | Roller et al. |
| 8,753,375 B2 | 6/2014 | Albertorio |
| 8,790,370 B2 | 7/2014 | Spenciner et al. |
| 8,808,329 B2 | 8/2014 | Bonutti |
| 8,814,905 B2 | 8/2014 | Sengun et al. |
| 8,821,544 B2 | 9/2014 | Sengun et al. |
| 8,821,545 B2 | 9/2014 | Sengun |
| 8,876,900 B2 | 11/2014 | Guederian et al. |
| 8,882,816 B2 | 11/2014 | Kartalian et al. |
| 8,888,815 B2 | 11/2014 | Holmes, Jr. |
| 8,961,575 B2 | 2/2015 | Choinski |
| 8,998,904 B2 | 4/2015 | Zeetser et al. |
| 9,005,245 B2 | 4/2015 | Thornes et al. |
| 9,072,510 B2 | 7/2015 | Thornes et al. |
| 2002/0029066 A1 | 3/2002 | Foerster |
| 2002/0173788 A1* | 11/2002 | Bojarski ............ A61B 17/0401 606/60 |
| 2003/0178852 A1 | 9/2003 | McNicholas |
| 2004/0015171 A1 | 1/2004 | Bojarski et al. |
| 2004/0153153 A1 | 8/2004 | Elson et al. |
| 2005/0038427 A1 | 2/2005 | Perriello et al. |
| 2005/0288710 A1 | 12/2005 | Fallin et al. |
| 2006/0064126 A1 | 3/2006 | Fallin et al. |
| 2006/0089646 A1 | 4/2006 | Bonutti |
| 2006/0190042 A1 | 8/2006 | Stone et al. |
| 2007/0149980 A1 | 6/2007 | Seedhom et al. |
| 2007/0233241 A1 | 10/2007 | Graf et al. |
| 2008/0027446 A1 | 1/2008 | Stone et al. |
| 2008/0046009 A1 | 2/2008 | Albertorio et al. |
| 2008/0188935 A1 | 8/2008 | Saylor et al. |
| 2008/0287991 A1 | 11/2008 | Fromm |
| 2009/0038206 A1 | 2/2009 | Conte |
| 2009/0043318 A1 | 2/2009 | Michel et al. |
| 2009/0082805 A1 | 3/2009 | Kaiser et al. |
| 2009/0105754 A1 | 4/2009 | Sethi |
| 2009/0234377 A1 | 9/2009 | Mahlin et al. |
| 2009/0281568 A1 | 11/2009 | Cendan et al. |
| 2009/0312776 A1 | 12/2009 | Kaiser et al. |
| 2009/0312792 A1 | 12/2009 | Fallin et al. |
| 2010/0069926 A1 | 3/2010 | Goble et al. |
| 2010/0106194 A1 | 4/2010 | Bonutti et al. |
| 2010/0125297 A1 | 5/2010 | Guederian et al. |
| 2010/0249809 A1 | 9/2010 | Singhatat et al. |
| 2010/0256677 A1 | 10/2010 | Albertorio et al. |
| 2010/0268273 A1 | 10/2010 | Albertorio et al. |
| 2010/0292733 A1 | 11/2010 | Hendricksen et al. |
| 2010/0305585 A1 | 12/2010 | Fallin et al. |
| 2010/0318126 A1 | 12/2010 | Fallin et al. |
| 2010/0324676 A1 | 12/2010 | Albertorio et al. |
| 2011/0022061 A1 | 1/2011 | Orphanos et al. |
| 2011/0022083 A1 | 1/2011 | DiMatteo et al. |
| 2011/0060375 A1 | 3/2011 | Bonutti |
| 2011/0077667 A1 | 3/2011 | Singhatat et al. |
| 2011/0087280 A1 | 4/2011 | Albertorio |
| 2011/0098727 A1 | 4/2011 | Kaiser et al. |
| 2011/0106151 A1 | 5/2011 | McDevitt et al. |
| 2011/0118780 A1 | 5/2011 | Holmes, Jr. |
| 2011/0144699 A1 | 6/2011 | Fallin et al. |
| 2011/0152927 A1 | 6/2011 | Deng et al. |
| 2011/0160749 A1 | 6/2011 | Gordon et al. |
| 2011/0160856 A1 | 6/2011 | Sinnott et al. |
| 2011/0190815 A1 | 8/2011 | Saliman |
| 2011/0208240 A1 | 8/2011 | Stone et al. |
| 2011/0218625 A1 | 9/2011 | Berelsman et al. |
| 2011/0238111 A1 | 9/2011 | Frank |
| 2011/0276137 A1 | 11/2011 | Seedhom et al. |
| 2011/0301708 A1* | 12/2011 | Stone ................ A61B 17/0401 623/13.14 |
| 2012/0046693 A1 | 2/2012 | Denham et al. |
| 2012/0046747 A1 | 2/2012 | Justin et al. |
| 2012/0053630 A1 | 3/2012 | Denham et al. |
| 2012/0059416 A1 | 3/2012 | Justin et al. |
| 2012/0059468 A1 | 3/2012 | Mattern et al. |
| 2012/0065731 A1 | 3/2012 | Justin et al. |
| 2012/0065732 A1 | 3/2012 | Roller et al. |
| 2012/0109129 A1 | 5/2012 | Bernstein |
| 2012/0109194 A1 | 5/2012 | Miller et al. |
| 2012/0116452 A1 | 5/2012 | Stone et al. |
| 2012/0123474 A1 | 5/2012 | Zajac et al. |
| 2012/0123541 A1 | 5/2012 | Albertorio et al. |
| 2012/0150203 A1 | 6/2012 | Brady et al. |
| 2012/0150297 A1 | 6/2012 | Denham et al. |
| 2012/0158051 A1 | 6/2012 | Foerster |
| 2012/0158053 A1 | 6/2012 | Paulos |
| 2012/0165867 A1 | 6/2012 | Denham et al. |
| 2012/0165938 A1 | 6/2012 | Denham et al. |
| 2012/0290002 A1 | 11/2012 | Astorino |
| 2012/0290004 A1 | 11/2012 | Lombardo et al. |
| 2012/0290006 A1 | 11/2012 | Collins et al. |
| 2012/0296375 A1 | 11/2012 | Thal |
| 2012/0303059 A1 | 11/2012 | Saadat et al. |
| 2012/0310279 A1 | 12/2012 | Sikora et al. |
| 2013/0023942 A1 | 1/2013 | Wyman et al. |
| 2013/0035722 A1 | 2/2013 | McDevitt et al. |
| 2013/0066371 A1 | 3/2013 | Rogers et al. |
| 2013/0096612 A1 | 4/2013 | Zajac et al. |
| 2013/0123810 A1 | 5/2013 | Brown et al. |
| 2013/0123841 A1 | 5/2013 | Lyon |
| 2013/0138150 A1 | 5/2013 | Baker et al. |
| 2013/0165972 A1 | 6/2013 | Sullivan |
| 2013/0165973 A1 | 6/2013 | Fallin et al. |
| 2013/0172944 A1 | 7/2013 | Fritzinger et al. |
| 2013/0197576 A1 | 8/2013 | Catania et al. |
| 2013/0197577 A1 | 8/2013 | Wolf et al. |
| 2013/0197578 A1 | 8/2013 | Gregoire et al. |
| 2013/0197579 A1 | 8/2013 | Foerster et al. |

(56) References Cited

U.S. PATENT DOCUMENTS

| | | |
|---|---|---|
| 2013/0197580 A1 | 8/2013 | Perriello et al. |
| 2013/0268000 A1 | 10/2013 | Harner et al. |
| 2013/0268073 A1 | 10/2013 | Albertorio et al. |
| 2013/0289620 A1 | 10/2013 | McDevitt et al. |
| 2013/0317544 A1 | 11/2013 | Ferguson et al. |
| 2014/0074239 A1 | 3/2014 | Albertorio et al. |
| 2014/0081399 A1 | 3/2014 | Roller et al. |
| 2014/0142627 A1 | 5/2014 | Hendricksen et al. |
| 2014/0330312 A1 | 11/2014 | Spenciner et al. |
| 2015/0073477 A1 | 3/2015 | Holmes, Jr. |
| 2016/0157851 A1 | 6/2016 | Spenciner |

FOREIGN PATENT DOCUMENTS

| | | |
|---|---|---|
| WO | 1996/029029 A1 | 9/1996 |
| WO | 1998/012991 A1 | 4/1998 |
| WO | 1998/012992 A1 | 4/1998 |
| WO | 1999/047079 A1 | 9/1999 |
| WO | 2002/034166 A1 | 5/2002 |
| WO | 2004/062507 A2 | 7/2004 |
| WO | 2005/051242 A1 | 6/2005 |
| WO | 2005/051245 A2 | 6/2005 |
| WO | 2009/109778 A2 | 9/2009 |
| WO | 2012/047925 A2 | 4/2012 |
| WO | 2012/167138 A1 | 12/2012 |

OTHER PUBLICATIONS

Kamelger et al., Suspensory Fixation of Grafts in Anterior Cruciate; Ligament Reconstruction: A Biomechanical Comparison of 3 Implants. Arthroscopy, Jul. 25, 2009, pp. 767-776.

Petre et al., Femoral Cortical Suspension Devices for Soft Tissue Anterior Cruciate Ligament Reconstruction. The American Journal of Sports Medicine, Feb. 2013, pp. 416-422.

U.S. Appl. No. 14/986,584, filed Dec. 31, 2015, Implant Having Adjustable Filaments Coils.

* cited by examiner

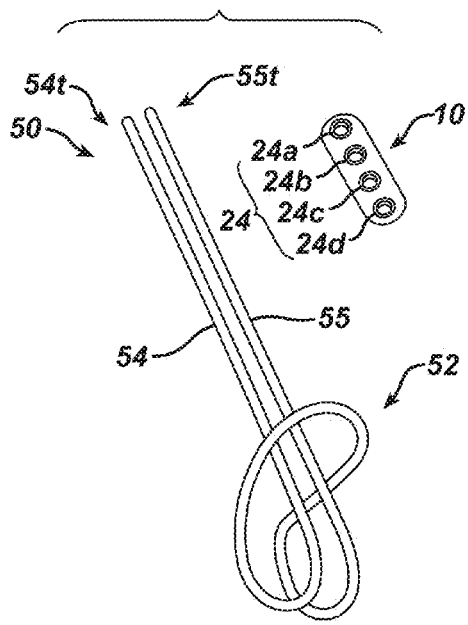
FIG. 1A
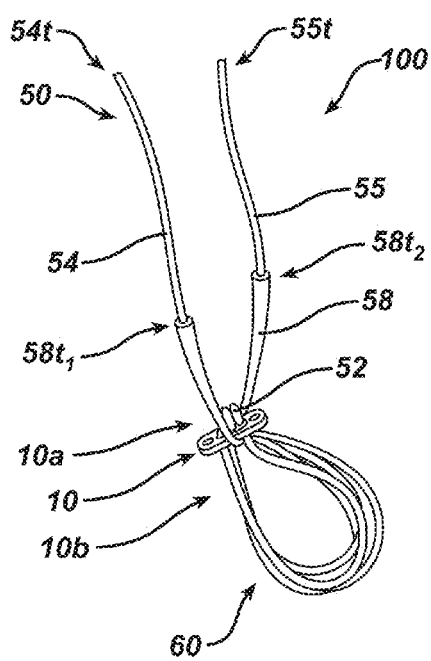
FIG. 1B
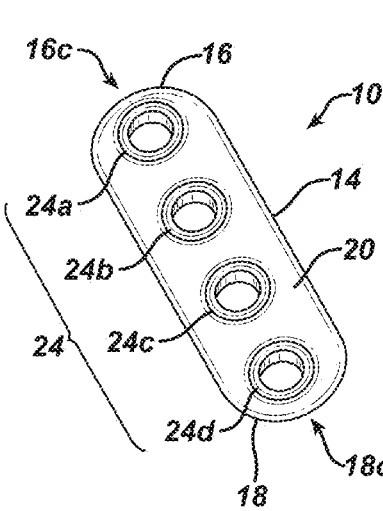
FIG. 2A
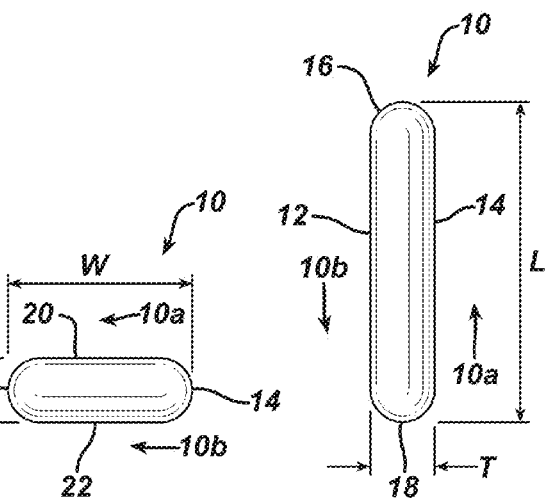
FIG. 2B      FIG. 2C

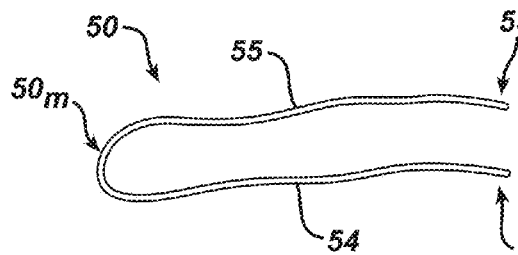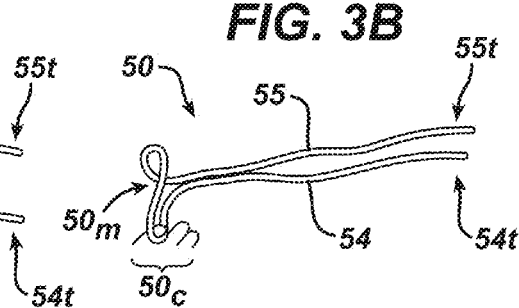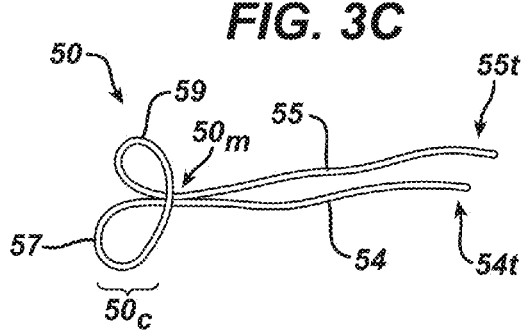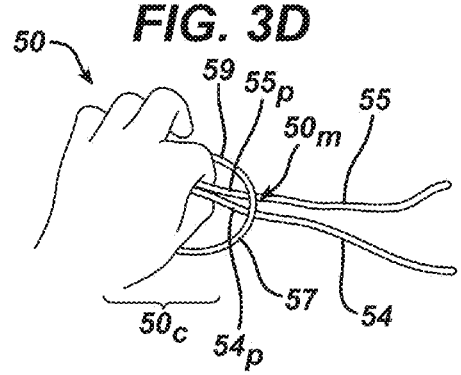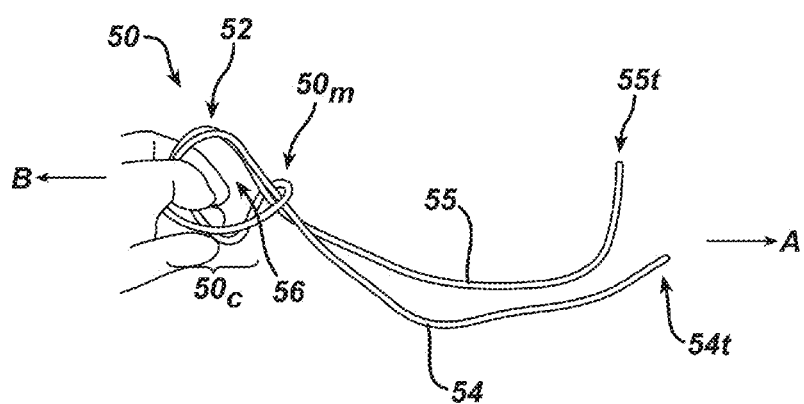

IMPLANT HAVING ADJUSTABLE FILAMENT COILS

FIELD

The present disclosure relates to devices, systems, and methods for securing soft tissue to bone, and more particularly it relates to securing an ACL graft to a femur.

BACKGROUND

Joint injuries may commonly result in the complete or partial detachment of ligaments, tendons, and soft tissues from bone. Tissue detachment may occur in many ways, e.g., as the result of an accident such as a fall, overexertion during a work related activity, during the course of an athletic event, or in any one of many other situations and/or activities. These types of injuries are generally the result of excess stress or extraordinary forces being placed upon the tissues.

In the case of a partial detachment, commonly referred to under the general term "sprain," the injury frequently heals without medical intervention, the patient rests, and care is taken not to expose the injury to undue strenuous activities during the healing process. If, however, the ligament or tendon is completely detached from its attachment site on an associated bone or bones, or if it is severed as the result of a traumatic injury, surgical intervention may be necessary to restore full function to the injured joint. A number of conventional surgical procedures exist for re-attaching such tendons and ligaments to bone.

One such procedure involves forming aligned femoral and tibial tunnels in a knee to repair a damaged anterior cruciate ligament ("ACL"). In one ACL repair procedure, a ligament graft is associated with a surgical implant and secured to the femur. A common ACL femoral fixation means includes an elongate "button," sometimes referred to as a cortical button. The cortical button is attached to a suture loop that is sized to allow an adequate length of a soft tissue graft to lie within the femoral tunnel while providing secure extra-cortical fixation.

Existing devices and methods can be limited because they do not always provide the desired strength. In some instances, one or more knots tied to help maintain a location of the suture loop with respect to a cortical button, and thus the graft associated therewith, can loosen or slip. Thus, even if a ligament graft is disposed at a desired location during a procedure, post-operatively the circumference of the loop can increase, causing the graft to move away from the desired location. Further, it can be desirable to limit the number of knots used in conjunction with such devices, because of the potential for the knots loosening and because the additional surface area knots can increase the risk of trauma. Still further, existing devices and methods also lack adjustability in many instances. For example, in procedures in which multiple ligament grafts are associated with the cortical button, it can be difficult to control placement of one ligament graft without also moving the other ligament graft.

Accordingly, it is desirable to provide devices, systems, and methods that improve the strength and adjustability of surgical implants used in conjunction with ligament graft insertion, and to minimize the number of knots associated with maintaining a location of the grafts once the grafts are disposed at desired locations.

SUMMARY

Devices, systems, and methods are generally provided for performing ACL repairs. In one exemplary embodiment, a surgical implant includes a body having a plurality of thru-holes and a suture filament extending through the body. The filament can be configured to form a knot and a plurality of coils, with the knot being located on a top side of the body and a portion of each coil being disposed on both the top side of the body and a bottom side of the body as a result of the filament being disposed through at least two of the plurality of thru-holes of the body. The knot can be a self-locking knot, with the self-locking knot defining a collapsible opening. The knot can have a portion of the suture filament that is intermediate its first terminal end and the plurality of coils and is disposed on the top side of the body passed through the collapsible opening from a first side of the opening. Further, the knot can have a portion of the suture filament that is intermediate its second terminal end and the plurality of coils and disposed on the top side of the body passed through the collapsible opening from a second, opposite side of the opening. In some embodiments, the collapsible opening can be configured to collapse and move toward the body when tension is applied to at least one of the first and second terminal ends.

The plurality of coils can include a first coil and a second coil formed by a first portion of the filament extending between the self-locking knot and the first terminal end, and a third coil and a fourth coil formed by a second portion of the filament extending between the self-locking knot and the second terminal end. In some embodiments the thru-holes of the body include two outer thru-holes and two inner thru-holes, with each outer thru-hole being located adjacent to respective opposed terminal ends of the body and the inner thru-holes being disposed between the outer thru-holes. In such embodiments, the first and third coils can pass through each of the outer thru-holes and the second and fourth coils can pass through each of the inner thru-holes. Alternatively, in such embodiments, the first, second, third, and fourth coils can all pass through each of the inner thru-holes. At least one coil can be configured such that its circumference can be changed by applying tension to at least one of the first and second terminal ends. In some embodiments the plurality of coils can be configured such that a circumference of one coil can be adjusted independent from adjusting a circumference of another coil.

The self-locking knot can include a Lark's Head knot. The Lark's Head knot can have certain modifications or additions to allow it to be self-locking, as described in greater detail herein. In some embodiments the implant can include a second suture filament extending longitudinally through the body. The second suture filament can pass through each thru-hole of the plurality of thru-holes, and can be used, for example, as a shuttle to help guide the implant through a bone tunnel.

A sleeve can be included as part of the implant. A sleeve can be disposed over a first portion of the suture filament that extends between the self-locking knot and the first terminal end, and a sleeve can be disposed over a second portion of the suture filament that extends between the self-locking knot and the second terminal end, with each sleeve being located on the top side of the body. In some embodiments the sleeve disposed over the first portion and the sleeve disposed over the second portion can be the same sleeve, with a portion of that sleeve being disposed around the bottom side of the body.

Another exemplary embodiment of a surgical implant includes a body having a plurality of thru-holes formed therein and a suture filament attached to the body such that the filament has a first terminal end, a second terminal end, and a Lark's Head knot formed therein, all of which are located on a top side of the body. The suture filament can be arranged with respect to the body such that a first portion of the filament extending between the Lark's Head knot and the first terminal end passes through one thru-hole to a bottom side of the body and through a different thru-hole to the top side of the body to form a first loop. Similarly, a second portion of the filament extending between the Lark's Head knot and the second terminal end passes through one thru-hole to the bottom side of the body and through a different thru-hole to the top side of the body to form a second loop. Further, the first terminal end can pass through an opening defined by the Lark's Head knot from a first side of the opening and the second terminal end can pass through the same opening from a second, opposite side of the opening.

In some embodiments, additional loops can be formed from the suture filament. For example, the suture filament can be arranged with respect to the body such that its first portion passes through one thru-hole to the bottom side of the body and through a different thru-hole to the top side to form a third loop, while its second portion passes through one thru-hole to the bottom side of the body and through a different thru-hole to the top side to form a fourth loop. In some embodiments the thru-holes of the body include two outer thru-holes and two inner thru-holes, with each outer thru-hole being located on an outer portion of the body and the inner thru-holes being disposed between the outer thru-holes. In such embodiments, the first and second portions of the suture filament can pass through each of the outer thru-holes and through each of the inner thru-holes at least once. Alternatively, in such embodiments, the first and second portions of the suture filament can pass through each of the inner thru-holes at least twice. A length of the filament's first portion and a length of the filament's second portion can be adjustable. In some embodiments the implant can include a second suture filament extending longitudinally through the body. The second suture filament can pass through each thru-hole of the plurality of thru-holes, and can be used, for example, as a shuttle to help guide the implant through a bone tunnel.

One exemplary embodiment of a surgical method includes loading a graft onto one or more coils of a plurality of coils of an implant filament that is coupled to an implant body, pulling a leading end of a shuttle filament that is disposed through the implant body through a bone tunnel until the implant body is pulled out of the tunnel while at least a portion of the implant filament and the graft remain in the tunnel, and orienting the implant body so that its bottom side is facing the bone tunnel through which the implant body passed. Pulling the leading end of the shuttle filament also necessarily pulls the implant body, the implant filament, and the graft through the tunnel. The resulting orientation of the implant's bottom side facing the tunnel is such that the plurality of coils are disposed substantially within the tunnel and a sliding knot first and second terminal ends of the implant filament are located outside of the tunnel, adjacent to a top side of the implant body.

In some embodiments, the step of orienting the implant body can be performed by pulling a trailing end of the shuttle filament. Alternatively, the step of orienting the implant body can be performed by pulling both the leading and trailing ends of the shuttle filament. The method can further include selectively applying tension to at least one of the first and second terminal ends to adjust a circumference of one or more of the coils.

BRIEF DESCRIPTION OF DRAWINGS

This invention will be more fully understood from the following detailed description taken in conjunction with the accompanying drawings, in which:

FIG. 1A is a schematic view of components of one exemplary embodiment of a surgical implant, including a cortical button and a suture filament having a Lark's Head knot formed therein;

FIG. 1B is a perspective side view of one exemplary embodiment of a surgical implant formed using the cortical button and suture filament of FIG. 1A;

FIG. 2A is a top perspective view of the cortical button of FIG. 1A;

FIG. 2B is an end elevational view of the cortical button of FIG. 2A;

FIG. 2C is a side elevational view of the cortical button of FIG. 2A;

FIGS. 3A-3E are sequential views illustrating one exemplary embodiment for forming the Lark's Head knot of FIG. 1A;

DETAILED DESCRIPTION

Figure 4:
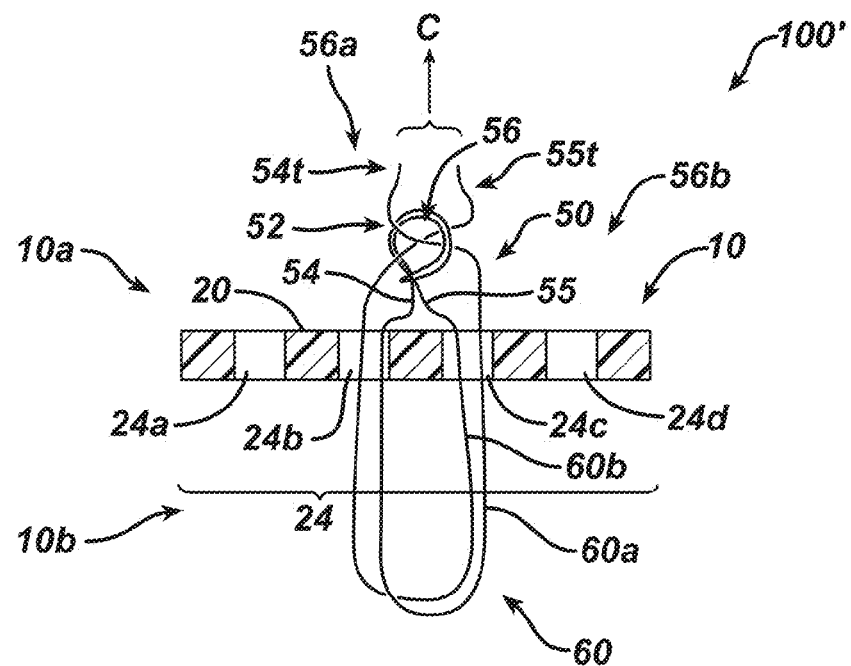
FIG. 4 is a schematic side cross-sectional view of one exemplary embodiment of a surgical implant.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Further, in the present disclosure, like-numbered components of the embodiments generally have similar features. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

The figures provided herein are not necessarily to scale. Further, to the extent arrows are used to describe a direction a component can be tensioned or pulled, these arrows are illustrative and in no way limit the direction the respective component can be tensioned or pulled. A person skilled in the art will recognize other ways and directions for creating the desired tension or movement. Likewise, while in some embodiments movement of one component is described with respect to another, a person skilled in the art will recognize that other movements are possible. By way of non-limiting example, in embodiments in which a sliding knot is used to help define a collapsible loop, a person skilled in the art will recognize that different knot configurations can change whether moving the knot in one direction will cause a size of an opening defined by the knot will increase or decrease. Additionally, a number of terms may be used throughout the disclosure interchangeably but will be understood by a person skilled in the art. By way of non-limiting example, the terms "suture" and "filament" may be used interchangeably.

The present disclosure generally relates to a surgical implant for use in surgical procedures such as ACL repairs. The implant can include a body having thru-holes formed therein and a suture filament associated therewith. An exemplary embodiment of a body 10 and a suture filament 50 illustrated separately is shown in FIG. 1A, while an exemplary embodiment of the two components coupled together to form an implant 100 is shown in FIG. 1B. The suture filament 50 can form a self-locking knot 52, illustrated as including a Lark's Head knot in FIG. 1A, and first and second tails 54, 55 extending therefrom can be passed through thru-holes 24 formed in the body 10 to associate the two components. As described below, the self-locking knot 52 is actually a Lark's Head knot modified to make it self-locking.

While the particulars of the formation of the construct illustrated in FIG. 1B are discussed in greater detail below, as shown the self-locking knot 52 can be formed on a first, top side 10a of the body 10 and a plurality of coils 60 formed from the first and second tails 54, 55 extending from the self-locking knot 52 can be disposed on a second, bottom side 10b of the body 10. First and second terminal ends 54t, 55t of the first and second tails 54, 55 can be passed through a collapsible opening 56 (FIGS. 4 and 5) of the self-locking knot 52 before the knot 52 is collapsed, with the second terminal end 55t passing through the collapsible opening 56 from a first side 56a of the opening 56, and the first terminal end 54t passing through the collapsible opening 56 from a second, opposite side 56b of the opening 56. As shown, the terminal ends 54t, 55t can extend proximally from the self-locking knot 52, and the collapsible opening 56 can be configured to collapse and move toward the body 10 when tension is applied to at least one of the terminal ends 54t, 55t. Applying tension to the terminal ends 54t, 55t can also selectively adjust a circumference of one or more of the coils 60 without adjusting a circumference of all of the coils 60. Optionally, a sleeve 58 can be associated with one or both of the tail portions extending between the self-locking knot 52 and the first and second terminal ends 54t, 55t. The sleeve 58 can help prevent the tails 54, 55 from being cut too close to the knot 52 after a desired implant location is achieved.

A body 10 for use as a part of a surgical implant to fixate a ligament graft in bone is illustrated in FIGS. 2A-2C. The body 10 can have a somewhat rectangular, elongate shape with curved leading and trailing terminal ends 16, 18. A plurality of thru-holes 24 can extend from a first, top surface 20 and through a second, bottom surface 22. In the illustrated embodiment there are two outer thru-holes 24a, 24d disposed, respectively, adjacent to leading and trailing terminal ends 16, 18, and two inner thru-holes 24b, 24c disposed between the two outer holes 24a, 24d. As shown, the outer and inner thru-holes 24a, 24d and 24b, 24c have diameters that are substantially the same, and a space separating adjacent thru-holes 24 is substantially the same for each adjacent pair. A width W of the body 10 is defined by the distance between the two elongate sidewalls 12, 14, as shown in FIG. 2B, a length L of the body 10 is defined by the distance between central portions 16c, 18c of the end walls of the leading and trailing terminal ends 16, 18, as shown in FIG. 2C, and a thickness T of the body 10 is defined by the distance between the top and bottom surfaces 20, 22, as shown in FIGS. 2B and 2C. The body 10 can generally be referred to as a cortical button, among other known terms.

A person skilled in the art will recognize that the body 10 described herein is merely one example of a body that can be used in conjunction with the teachings provided herein. A body configured to be associated with a suture filament of the type described herein can have a variety of different shapes, sizes, and features, and can be made of a variety of different materials, depending, at least in part, on the other components with which it is used, such as the suture filament and the ligament graft, and the type of procedure in which it is used. Thus, while in the present embodiment the body 10 is somewhat rectangular having curved ends, in other embodiments the body can be substantially tubular, among other shapes.

In one exemplary embodiment of the substantially rectangular button, the length L of the body is in the range of about 5 millimeters to about 30 millimeters, the width W is in the range of about 1 millimeter to about 10 millimeters, and the thickness T is in the range of about 0.25 millimeters to about 3 millimeters. In one exemplary embodiment, the length L can be about 12 millimeters, the width W can be about 4 millimeters, and the thickness T can be about 1.5 millimeters. Diameters of the thru-holes 24 can be in the range of about 0.5 millimeters to about 5 millimeters, and in one exemplary embodiment each can be about 2 millimeters. Although in the illustrated embodiment each of the thru-holes 24a, 24b, 24c, 24d has a substantially similar diameter, in other embodiments some of the thru-holes can have different diameters. Additionally, any number of thru-holes can be formed in the body 10, including as few as two.

In exemplary embodiments the body 10 can be made from a stainless steel or titanium, but any number of polymers, metals, or other biocompatible materials in general can be used to form the body. Some non-limiting examples of biocompatible materials suitable for forming the body include a polyether ether ketone (PEEK), bioabsorbable elastomers, copolymers such as polylactic acid-polyglycolic acid (PLA-PGA), and bioabsorbable polymers such as polylactic acid. The implant can also be formed of absorbable and non-absorbable materials. Other exemplary embodiments of a body or cortical button that can be used in conjunction with the teachings herein are described at least in U.S. Pat. No. 5,306,301 of Graf et al., the content of which is incorporated by reference herein in its entirety.

Steps for configuring the suture filament 50 for use as a part of the surgical implant 100 to fixate a ligament graft in bone are illustrated in FIGS. 3A-3E. As shown in FIG. 3A, the filament can be folded substantially in half at an approximate midpoint 50m of the filament 50, forming a first filament limb 54 and a second filament limb 55 having first and second terminal ends 54t and 55t, respectively. A central portion 50c of the filament 50, which includes the midpoint 50m, can be folded toward the first and second limbs 54, 55, as shown in FIG. 3B, and be brought proximate to the first and second limbs 54, 55. This results in the formation of a first secondary loop 57 and a second secondary loop 59, as shown in FIG. 3C. A size of the secondary loops 57, 59, and a length of the limbs 54, 55 extending therefrom, can be adjusted as desired.

As shown in FIG. 3D, a portion 54p, 55p of the first and second limbs 54, 55 that are part of the secondary loops 57, 59 can be grasped and pulled upward (as shown, "out of the page"). This results in the configuration illustrated in FIG. 3E, a filament having a Lark Head's knot 52 formed therein with first and second filament limbs 54, 55 having terminal ends 54t, 55t extending therefrom. The Lark's Head knot 52 defines a collapsible opening 56, a size of which can be decreased by applying a force in an approximate direction A to one or both of the limbs 54, 55 extending from the knot 52, or by applying a force in an approximate direction B to the opening 56. Likewise, a size of the opening 56 can be increased by grasping near the midpoint 50m of the filament 50 to hold the portion where the fold is formed approximately stationary and then applying either a force in the approximate direction B to both of the limbs 54, 55 extending from the knot 52, or a force in the approximate direction B to the opening 56. As described in greater detail below, the Lark's Head knot can be modified to form a self-locking knot.

A person skilled in the art will recognize other ways by which a Lark's Head knot can be formed. Similarly, a person skilled in the art will be familiar with other types of knots that can be formed in suture filaments, and will understand ways in which other knots can be adapted for use in a manner as the Lark's Head knot is used in the present disclosure. The present disclosure is not limited to use only with a Lark's Head knot.

The suture filament 50 can be an elongate filament, and a variety of different types of suture filaments can be used, including but not limited to a cannulated filament, a braided filament, and a mono filament. The type, size, and strength of the filament can depend, at least in part, on the other materials of the implant, including the material(s) of the cortical button and the ligament graft, the tissue, bone, and related tunnels through which it will be passed, and the type of procedure in which it is used. In one exemplary embodiment the filament is a #0 filament (about 26 gauge to about 27 gauge), such as an Orthocord™ filament that is commercially available from DePuy Mitek, LLC., 325 Paramount Drive, Raynham, Mass. 02767, or an Ethibond™ filament that is commercially available from Ethicon, Inc., Route 22 West, Somerville, N.J. 08876. The thickness of the filament should provide strength in the connection but at the same time minimize the trauma caused to tissue through which it passes. In some embodiments the filament can have a size in the range of about a #5 filament (about 20 gauge to about 21 gauge) to about a #3-0 filament (about 29 gauge to about 32 gauge). Orthocord™ suture is approximately fifty-five to sixty-five percent PDS™ polydioxanone, which is bioabsorbable, and the remaining thirty-five to forty-five percent ultra high molecular weight polyethylene, while Ethibond™ suture is primarily high strength polyester. The amount and type of bioabsorbable material, if any, utilized in the filaments of the present disclosure is primarily a matter of surgeon preference for the particular surgical procedure to be performed. In some exemplary embodiments, a length of the filament can be in the range of about 0.2 meters to about 5 meters, and in one embodiment it has a length of about 1.5 meters.

FIG. 4 illustrates one exemplary embodiment of the suture filament 50 being associated with the body 10 to form a surgical implant 100'. As shown, the Lark's Head knot 52 is disposed on a first, top side 10a of the body 10, and the limbs 54, 55 extending therefrom are used to associate the filament 50 with the body 10. The limbs 54, 55 can be selectively passed through one of the thru-holes 24 to a bottom side 10b of the body 10, and then through another of the thru-holes 24 back to the top side 10a. In the illustrated embodiment, the first limb 54 passes through the second thru-hole 24b to reach the bottom side 10b and then through the third thru-hole 24c to reach the top side 10a, while the second limb 55 passes through the third thru-hole 24c to reach the bottom side 10b and then through the second thru-hole 24b to reach the top side 10a, forming a coil or loop 60a of the first limb 54 and a coil or loop 60b of the second limb 55. The terminal ends 54t, 55t of the limbs 54, 55 can then be passed through the opening 56 defined by the Lark's Head knot 52. As shown, the terminal end 54t can be passed from the second side 56b of the opening 56, as shown a right side, through the opening 56, and to a first side 56a of the opening 56, as shown a left side, while the terminal end 55t can be passed from the first side 56a, through the opening 56, and to the second, opposite side 56b. The limbs 54, 55 can continue to be pulled through the opening 56 until a desired coil size for each of the first and second limbs 54, 55 is achieved. In alternative embodiments, one or both of the limbs 54, 55 can be passed through the opening 56 multiple times before using the limbs 54, 55 to adjust the coils 60 to the desired size.

Once the terminal ends 54t, 55t have been passed through the opening 56 and the desired coil size has been achieved, the opening 56 can be collapsed. One way that the opening 56 can be collapsed is by applying a force to the terminal ends 54t, 55t in an approximate direction C as shown, while also applying a counterforce to the coils 60 to approximately maintain the circumference of the coils. Without the counterforce, the force in the approximate direction C would typically decrease the circumference of the coils 60 before collapsing the opening 56. Because the terminal ends 54t, 55t are passed through opposing sides 56a, 56b of the opening 56, and compression of the Lark's Head knot 52 against a top surface 20 of the body 10 creates resistance against loosening, the resulting collapsed knot is self-locking, meaning the Lark's Head knot 52 is a sliding knot that locks itself without the aid of additional half-hitches or other techniques known to help secure a location of a knot with respect to the body 10.

After the opening 56 is collapsed, a circumference of the coils 60 can again be decreased by applying force to the terminal ends 54t, 55t in the approximate direction C with the first terminal end 54t generally controlling the size of the coil 60a and the second terminal end 55t generally controlling the size of the coil 60b. Because the collapsible opening 56 is self-locking, it can be more difficult to increase a circumference of the coils 60a, 60b after the opening 56 is collapsed. However, a person skilled in the art will understand how portions of the filament 50 that form the collapsible knot 52 can be manipulated to allow for increases in the circumference of the coils 60a, 60b.

Figure 5:
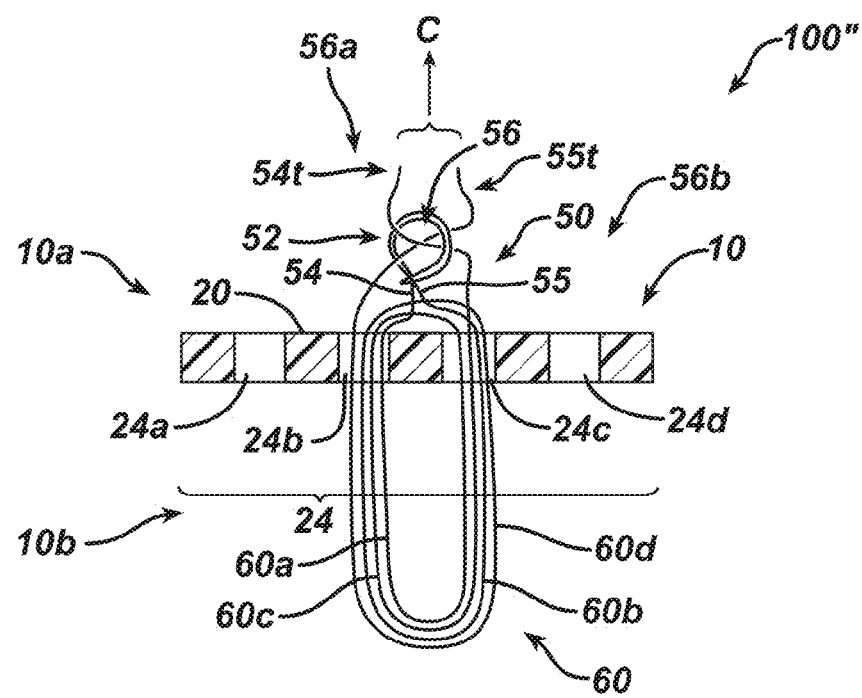
FIG. 5 is a schematic side cross-sectional view of another exemplary embodiment of a surgical implant.

In other embodiments, more than one coil can be formed by the first or second filament limbs. One exemplary embodiment of such an implant 100" is shown in FIG. 5. Similar to the implant 100', the Lark's Head knot 52 is disposed on the top side 10a of the body 10, and the limbs 54, 55 extending therefrom are selectively passed through multiple thru-holes 24 of the body 10 to associate the filament 50 with the body 10. In the illustrated embodiment, the first limb 54 passes distally through the second hole 24b to the bottom side 10b of the body 10, and through the third thru-hole 24c back to the top side 10a twice to form a first coil 60a and a second coil 60c before it is then passed through the opening 56 defined by the Lark's Head knot 52 from the second side 56b of the opening 56 to the first side 56a. Similarly, the second limb 55 passes distally through the third hole 24c to the bottom side 10b, and through the second thru-hole 24b back to the top side 10a twice to form a first coil 60b and a second coil 60d before it is then passed through the opening 56 from the first side 56a to the second side 56b. The opening 56 can be collapsed, and a circumference of the first and second coils 60a, 60c can be adjusted by the terminal end 54t and the first and second coils 60b, 60d can be adjusted by the terminal end 55t in manners similar to those described above with respect to the device 100'. The inclusion of a second coil formed from the limbs 54, 55 increases the strength of the implant 100" due to a pulley effect, allowing the implant 100" to be more stable when it is implanted in bone and to more stably hold a ligament graft attached to one or more of the coils 60.

Any number of coils can be formed from the first and second limbs 54, 55, and the number of coils formed in the first limb 54 does not have to be the same number of coils formed in the second limb 55. In some exemplary embodiments, three or four coils can be formed in one or both of the limbs. Further, the limbs used to form the coils can be passed through any number of thru-holes formed in the body 10. The first limb 54 does not need to pass through the same thru-holes through which the second limb 55 passes. Accordingly, by way of non-limiting example, a coil of the first limb 54 can be formed by passing the limb through the first thru-hole 24a and then back through the fourth thru-hole 24d and a coil of the second limb 55 can be formed by passing the limb through the third thru-hole 24c and then back through the second thru-hole 24b. By way of further non-limiting example, a coil of the first limb 54 can be formed by passing the limb through the second thru-hole 24b and then back through the fourth thru-hole 24d and a coil of the second limb 55 can be formed by passing the limb through the third thru-hole 24c and then back through the second-thru hole 24b.

Likewise, when multiple coils are formed in one limb, that limb does not have to be passed through the same thru-holes to form each coil. Accordingly, by way of non-limiting example, a first coil of the first limb 54 can be formed by passing the limb through the second thru-hole 24b and then back through the third thru-hole 24c and a second coil of the first limb 54 can be formed by passing the limb through the first thru-hole 24a and then back through the fourth thru-hole 24d. By way of further non-limiting example, a first coil of the second limb 55 can be formed by passing the limb through the fourth thru-hole 24d and then back through the first thru-hole 24a and a second coil of the second limb 55 can be formed by passing the limb through the fourth thru-hole 24d and then back through the second thru-hole 24b. In yet one further non-limiting example, a coil of the first limb 54 can be passed through the second thru-hole 24b and then back through the second thru-hole 24b and a coil of the second limb 55 can be passed through the third thru-hole 34c and then back through the third thru-hole 24c, with the first limb 54 and the second limb 55 intersecting at least once on the bottom side 10b so that the limbs 54, 55 remain on the bottom side 10b when they are passed back through the same thru-hole they came to reach the bottom side 10b in the first place. A person skilled in the art will recognize a number of configurations between the filament and thru-holes that can be used to form one or more coils in the filament limbs before disposing terminal ends of the limbs through a collapsible opening of a knot to create a self-locking knot.

A variety of tests were performed to assess the strength and integrity of an implant having a self-locking knot and four coils like some of the embodiments provided for herein. In particular, the tests were performed on the implant 100 shown in FIG. 2, with the filament being a braided #2 ultra high molecular weight polyethylene suture with a loop circumference of approximately 40 millimeters. Three separate cycle tests of varying length were performed. Generally, a cyclical load was applied to the implant 100 a plurality of times, with the load cycling between about 50 Newtons and about 250 Newtons. After a certain number of cycles were performed, the distance a graft migrated from its original position was measured. After 10 cycles a displacement of the implant 100 was about 1.0 mm, after 750 cycles a displacement of the implant was about 1.4 millimeters, and after 1000 cycles a displacement of the implant was about 1.4 millimeters. Further details about testing protocols of this nature can be found in an article written by Kamelger et al., entitled "Suspensory Fixation of Grafts in Anterior Cruciate Ligament Reconstruction: A Biomechanical Comparison of 3 Implants," published in *Arthroscopy*, Jul. 25, 2009, pp. 767-776, and in an article written by Petre et al., entitled "Femoral Cortical Suspension Devices for Soft Tissue Anterior Cruciate Ligament Reconstruction," published in *The American Journal of Sports Medicine*, February 2013, pp. 416-422, the content of each which is incorporated by reference herein in its entirety. A person skilled in the art will recognize that the test results are dependent at least on the type and size of the filament of the implant.

Another test determined an ultimate failure load of the implant 100. The ultimate failure load measures the load at which the implant 100 fails. The ultimate failure load tested for the implant 100 was about 1322 Newtons. During the ultimate failure load test, the displacement at 450 Newtons was also measured, with displacement being about 2.0 millimeters. Still another test performed on the implant was a regression stiffness test, which plots the displacement of the implant in comparison to the load and a slope of the initial line is measured. The implant 100 demonstrated a regression stiffness of about 775 Newtons per millimeter. Again, a person skilled in the art will recognize that these test results are dependent at least on the type and size of the filament of the implant.

Figure 6A:
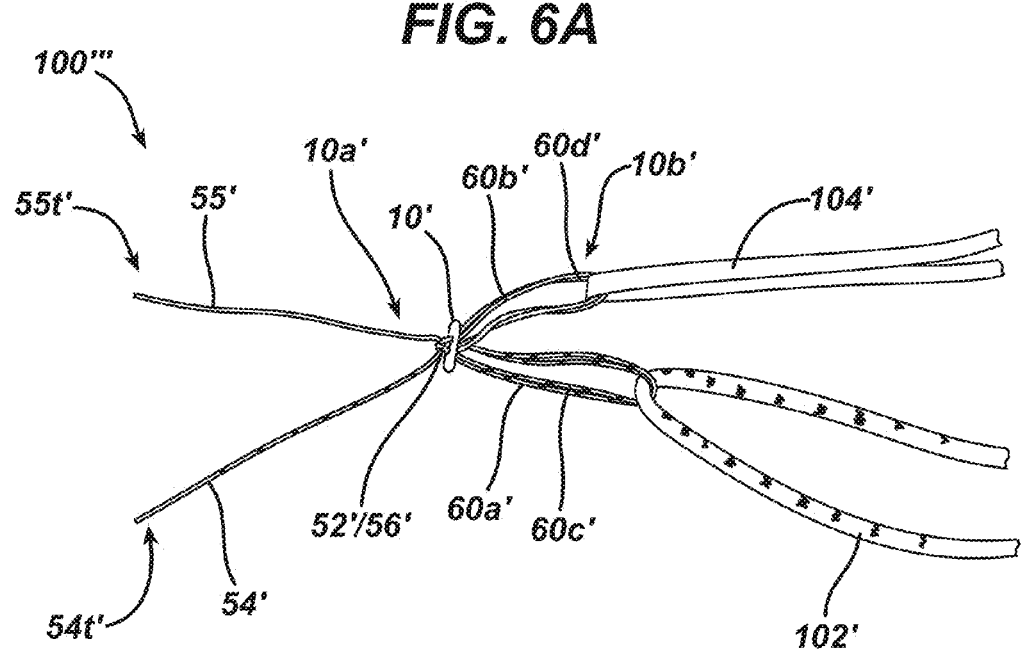
FIGS. 6A-6B are sequential view of yet another exemplary embodiment of a surgical implant, the implant having grafts associated therewith, illustrating selective movement of the grafts.
Figure 6B:
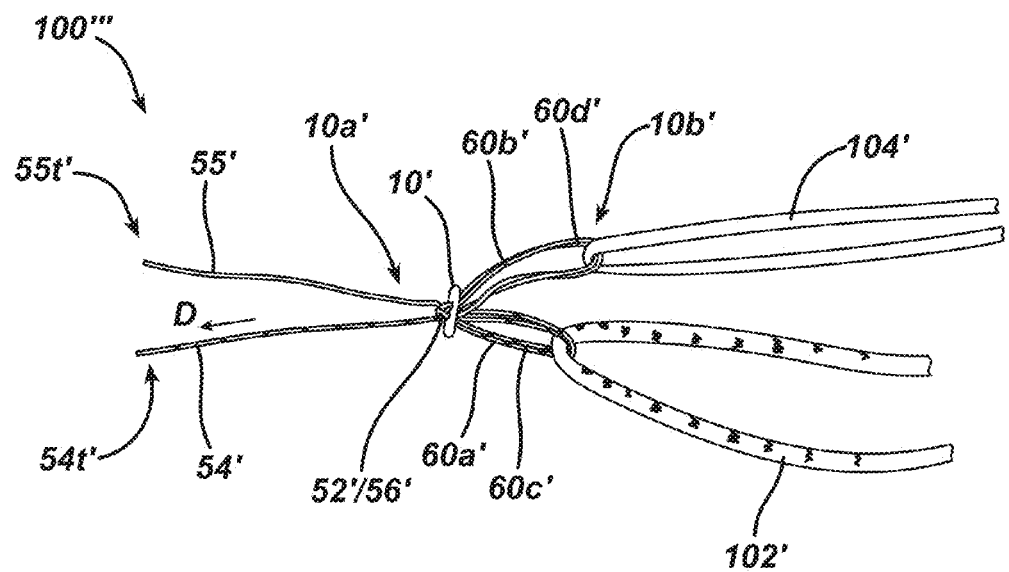

FIGS. 6A and 6B illustrate the ability to selectively control some coils 60a', 60c' of an implant 100''' using one limb 54' and other coils 60b', 60d' of the implant 100''' using the other limb 55'. As shown, the implant 100''' includes a single filament 50' associated with a body 10' having a plurality of thru-holes 24' formed therein. The configuration between the filament 50' and the body 10' is similar to the implants 100, 100'' described above with respect to FIGS. 2 and 5. As shown, a self-locking knot 52' is formed on a top side 10a' of the body 10' and four coils 60' are formed from first and second limbs 54', 55' extending from the self-locking knot 52', the four coils 60' being substantially disposed on a bottom side 10b' of the body 10'. Terminal ends 54t', 55t' of the first and second limbs 54', 55' pass through an opening 56' of the self-locking knot 52' before the knot is collapsed, and can be used to adjust a circumference of the coils 60'. In the illustrated embodiment, the first limb 54' is differentiated from the second limb 55' by including markings on the first limb 54'. These visual indicators allow a surgeon to easily know which coils are controlled by which limbs, and can be added to the filament before or after the filament is associated with the body 10'.

In the illustrated embodiment, a first ligament graft 102' is coupled to first and second coils 60a', 60c' of the first limb 54' by wrapping the graft 102' through each of the first and second coils 60a', 60c', and a second ligament graft 104' is coupled to first and second coils 60b', 60d' of the second limb 55' by wrapping the graft 104' through each of the first and second coils 60b', 60d'. As shown in FIGS. 6A and 6B, applying a force to the first limb 54' in an approximate direction D decreases the circumference of the first and second coils 60a', 60c', thereby drawing the first ligament graft 102' closer to the body 10'. More particularly, as tension is created by the force, the circumference of the diameter of the second coil 60c' decreases and advances the first graft 102'. As the distance between distal ends of the second coil 60c' and the first coil 60a' increases, the weight of the graft 102' helps create a counterforce that maintains the circumference of the second coil diameter while the circumference of the first coil 60a' decreases to catch-up to the second coil 60c' and the graft 102'. A person skilled in the art will understand how the application of various forces and tensions to the first and second limbs 54', 55', the first and second coils 60a', 60c' and 60b', 60d', and the first and second grafts 102', 104' associated therewith can be manipulated to selectively adjust locations of the grafts 102', 104' with respect to the body 10'.

As a result of this configuration, one ligament graft can be pulled closer the body 10' than another ligament graft. Such graft configurations can be useful to surgeons. By way of non-limiting example, if during the course of a tissue repair the surgeon accidentally amputated one of the hamstring tendons during harvesting or graft preparation, the coils associated with one of the terminal ends can be adjusted so that the longer tendon is pulled deeper into the femoral tunnel with the shorter tendon being more proximal of the longer tendon, thus leaving more graft for the tibial tunnel. By way of further non-limiting example, grafts can be independently tensioned such that they are tightest at different angles of knee flexion, which can provide superior biomechanics due to the repair being more anatomic. Other configurations that can permit selective, independent tightening of the coils formed in the suture filament can also be used while maintaining the spirit of the present disclosure. For example, two separate knot or finger-trap mechanisms can be disposed through the same thru-holes in the button to permit selective, independent control of the coils.

Figure 7A:
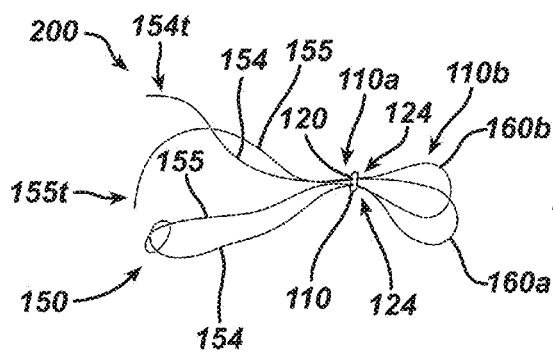
FIGS. 7A-7E are sequential views illustrating one exemplary embodiment of coupling a suture to a cortical button to form a surgical implant.

Two non-limiting alternative embodiments for associating a suture filament 150, 250 with a cortical button 110, 210 to form an implant 200, 300 are illustrated in FIGS. 7A-7E and FIGS. 8A-8H, respectively. Starting first with FIGS. 7A-7E, the cortical button 110 includes four thru-holes 124 disposed therein and the suture filament 150 is a braided suture. After forming a pretzel-shaped knot 152 using techniques known to those skilled in the art, first and second terminal ends 154t, 155t of the filament 150 can be passed through the two interior thru-holes 124 of the body 110, as illustrated in FIG. 7A, to form two loops or coils 160a, 160b for receiving a ligament graft. In this embodiment, both the first and second limbs 154, 155 pass through the same interior thru-hole 124 to pass from a top side 110a to a bottom side 110b of the body 110. Likewise, both limbs 154, 155 pass through the same interior thru-hole 124 to pass from the bottom side 110b back to the top side 110a.

Figure 7B:
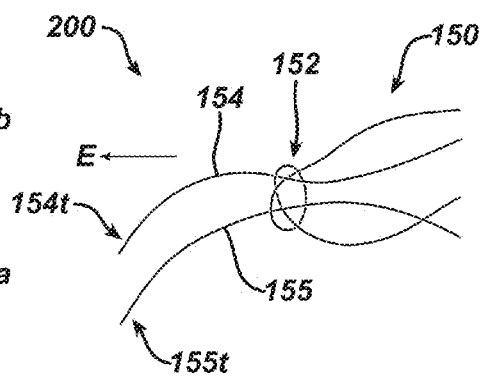
Figure 7C:
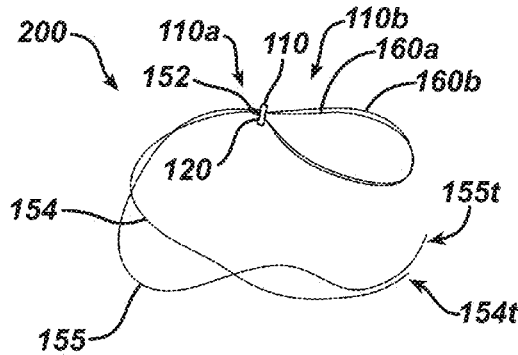
Figure 7D:
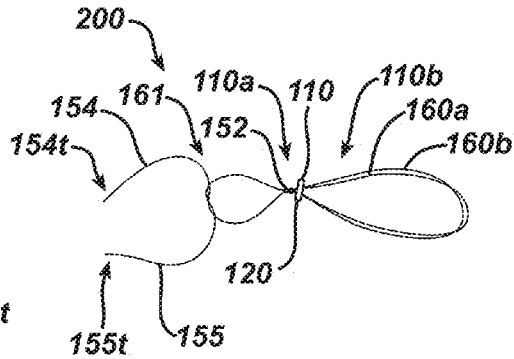

As shown in FIG. 7B, the terminal ends 154t, 155t can be passed through openings of the pretzel-shaped knot 152. Other suitable sliding knots can be used in lieu of a pretzel-shaped knot. Subsequently, a force can be applied to the terminal ends 154t, 155t in an approximate direction E to collapse and advance the knot 152 towards a top surface 120 of the body 110, as shown in FIG. 7C. The pretzel knot 152 is not generally self-locking. Accordingly, as shown in FIG. 7D, one or more half-hitches 161 can be formed in the terminal ends 154t, 155t to secure and lock a location of the collapsed pretzel knot 152 with respect to the body 110. A graft 202 can then be disposed within openings of the coils 160a, 160b formed by the first and second limbs 154, 155, as shown in FIG. 7E.

Figure 7E:
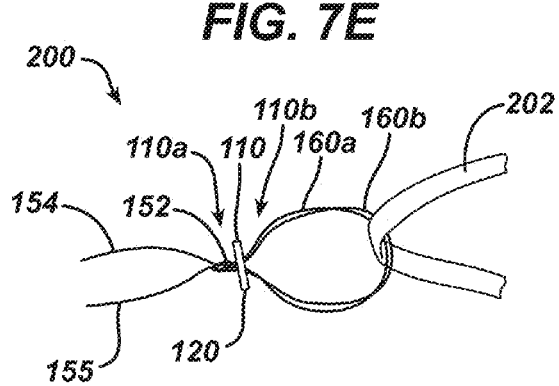

Tests performed using an implant like the embodiment shown in FIG. 7E, the filament being a braided #5 ultra high molecular weight polyethylene suture with a loop circumference of approximately 40 millimeters, yielded a $10^{th}$ cycle displacement of approximately 1.9 millimeters, a $750^{th}$ cycle displacement of approximately 2.2 millimeters, and a $1000^{th}$ cycle displacement of approximately 2.3 millimeters. The ultimate failure load was measured to be approximately 1521 Newtons. Displacement at a load of 800 Newtons was measured to be approximately 4.1 millimeters. Meanwhile, the regression stiffness was determined to be approximately 267 Newtons per millimeter. A person skilled in the art will recognize that the test results are dependent at least on the type and size of the filament of the implant.

Figure 8A:
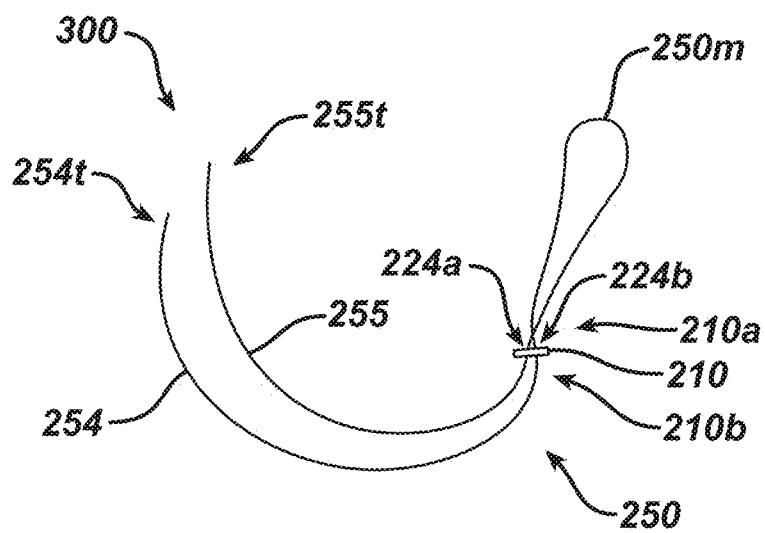
FIGS. 8A-8H are sequential views illustrating another exemplary embodiment of coupling a suture to a cortical button to form a surgical implant, and associating a graft therewith.
Figure 8B:
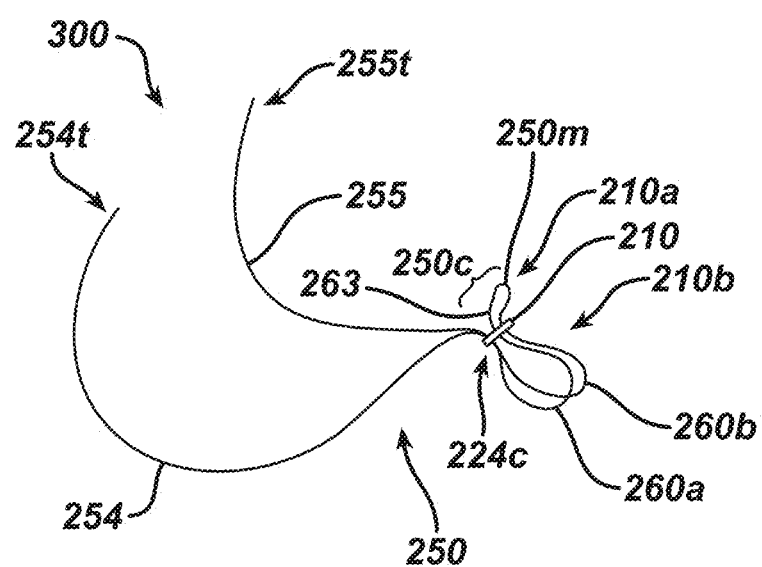

The embodiment illustrated in FIGS. 8A-8H also include a cortical button 210 having at least three thru-holes 224a, 224b, 224c disposed therein and a suture filament 250 that is a braided suture associated with the button 210 to form an implant 300. As shown in FIG. 8A, a terminal end 254t of a first limb 254 is passed from a top side 210a to a bottom side 210b of the body 210 through one of the thru-holes 224a and a terminal end 255t of a second limb 255 is passed from the top side 210a to the bottom side 210b through another thru-hole 224b. The two terminal ends 254t, 255t are then both passed back to the top side 210a through the third thru-hole 224c, as shown in FIG. 8B. The resulting configuration is a first loop 263 formed on the top side 210a from a central portion 250c of the filament 250 at an approximate midpoint 250m of the filament 250, and first and second coils 260a, 260b primarily located below the bottom side 210b.

Figure 8C:
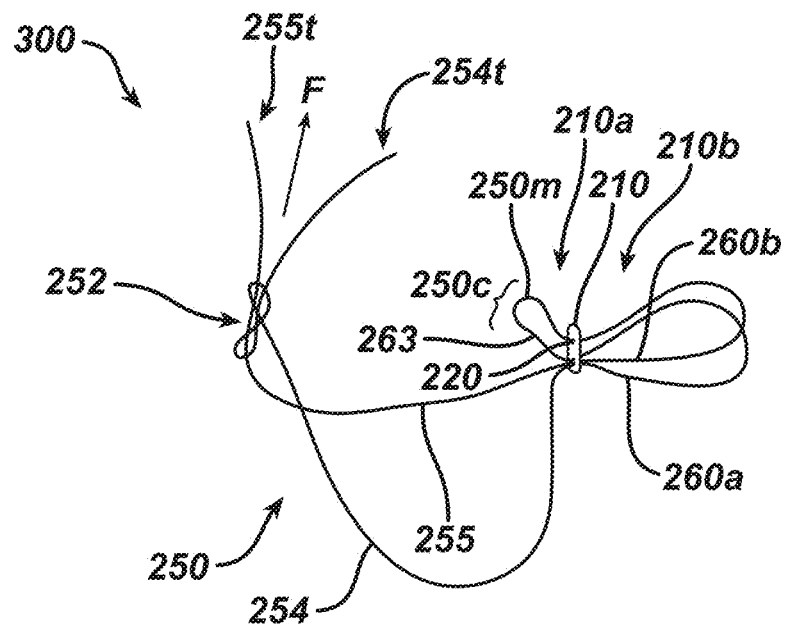
Figure 8D:
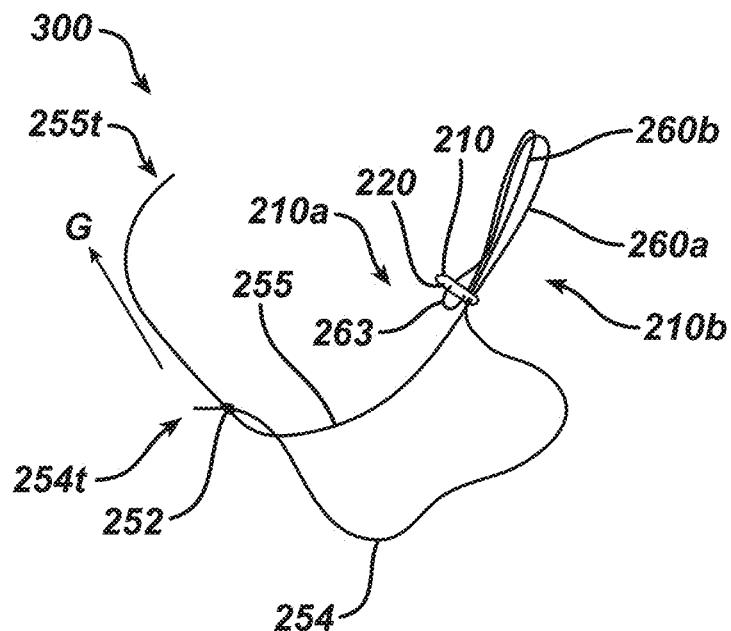
Figure 8E:
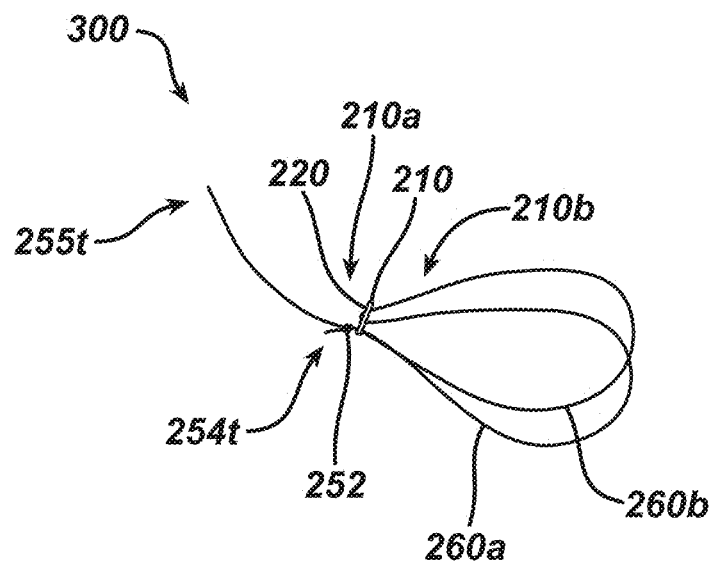

As shown in FIG. 8C, the terminal ends 254t, 255t can be formed into a sliding knot 252 such as a Buntline Hitch knot using techniques known to those skilled in the art. Other suitable sliding knots can be used in lieu of the Buntline Hitch knot. A force can then be applied in an approximate direction F to the terminal ends to tighten the Buntline Hitch knot, and as shown in FIG. 8D, the stationary terminal end, as shown the terminal end 254t, can be cut so that it is substantially shorter than the sliding terminal end extending proximally from the tightened sliding knot 252, as shown the terminal end 255t. The third thru-hole 224c can be sized such that the Buntline Hitch knot is too big to pass through it. Thus, a force in an approximate direction G can be applied to the longer sliding terminal end 255t to advance the knot 252 toward the body 210, and to collapse the first loop 263 against the top surface 220 of the body 210, as shown in FIG. 8E.

Figure 8F:
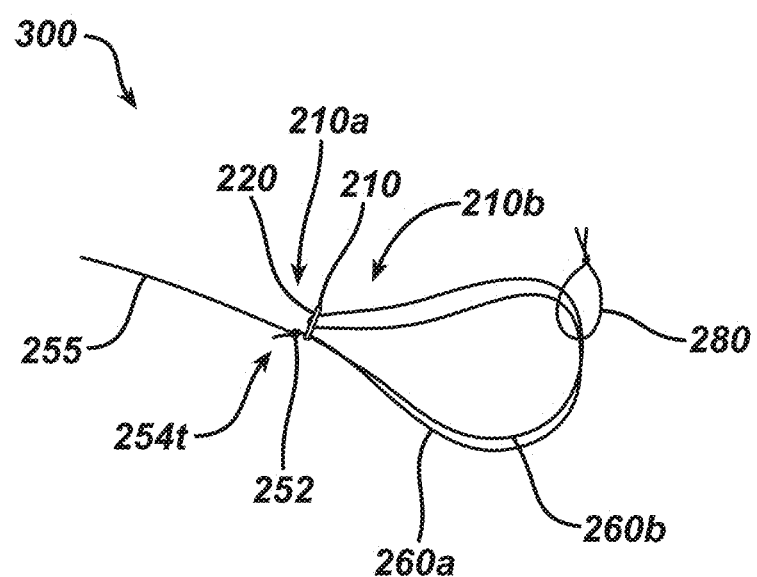
Figure 8G:
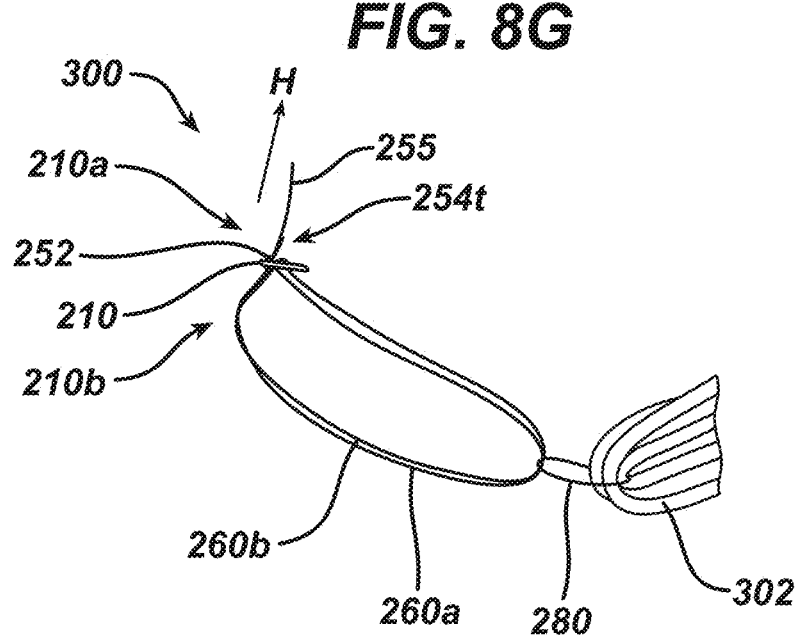
Figure 8H:
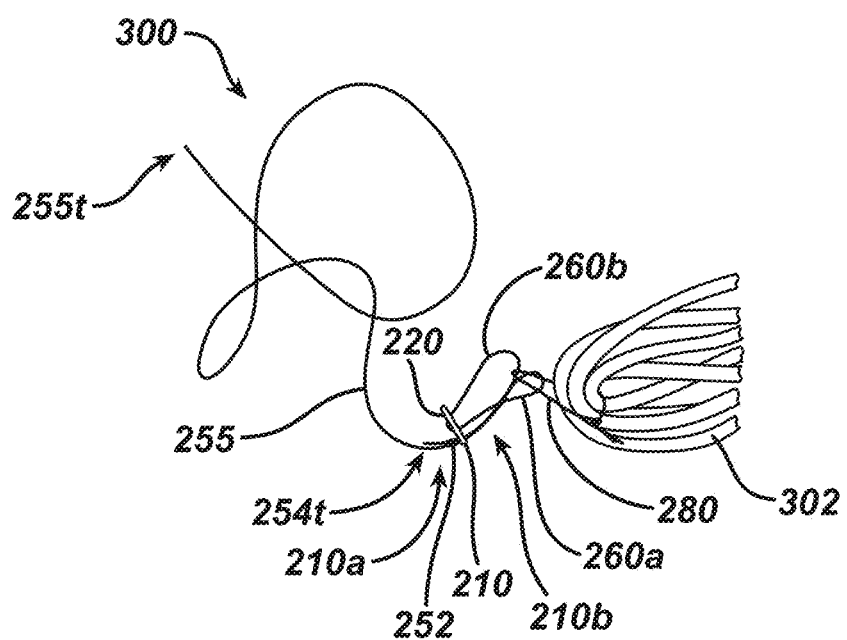

Optionally, a secondary loop 280 can be added to the first and second coils 260a, 260b, as shown in FIG. 8F. As shown, the secondary loop 280 is a closed, fixed loop having an approximately fixed circumference. The secondary loop 280 can be formed using any number of techniques known to those skilled in the art, but in the illustrated embodiment the secondary loop is disposed around the first and second coils 260a, 260b and tied together to form the closed, fixed loop. As shown in FIG. 8G, a ligament graft 302 can be disposed around the secondary loop 280. While in other embodiments the ligament graft was only disposed around the loop once, FIG. 8G illustrates that ligament grafts 302 can be disposed around a filament in any of the embodiments described herein multiple times. A force in an approximate direction H can then be applied to the long remaining terminal end 255t to decrease the circumference of the first and second coils 260a, 260b and advance the ligament graft 302 closer to the body 210, as shown in FIG. 8H.

In the embodiment illustrated in FIGS. 8A-8H, the ligament graft is not attached directly to coils 260a, 260b formed by the filament 250, but instead is coupled to the secondary loop 280. Such a secondary loop can be used in any of the embodiments described or derivable from disclosures made herein. In some embodiments the secondary loop can help minimize accidental graft damage due to wear with the main suture filament when the circumferences of the coils of the main filament are adjusted.

In some embodiments, including but not limited to those implants having a self-locking knot, a sleeve or spacer can be disposed over a portion of the first and second limbs on the top side of the body, adjacent to the top surface. The optional sleeve can assist in preventing a surgeon from cutting terminal ends of the limbs extending proximally from the knot too close to the body. The integrity of the knot, and thus the strength of the implant, can be compromised when the terminal ends of the limbs are cut too close to the body. The sleeve can generally have elastic properties such that it bunches as compressive forces are applied, and a surgeon can then cut the terminal ends at a location proximal of the sleeve.

Figure 9:
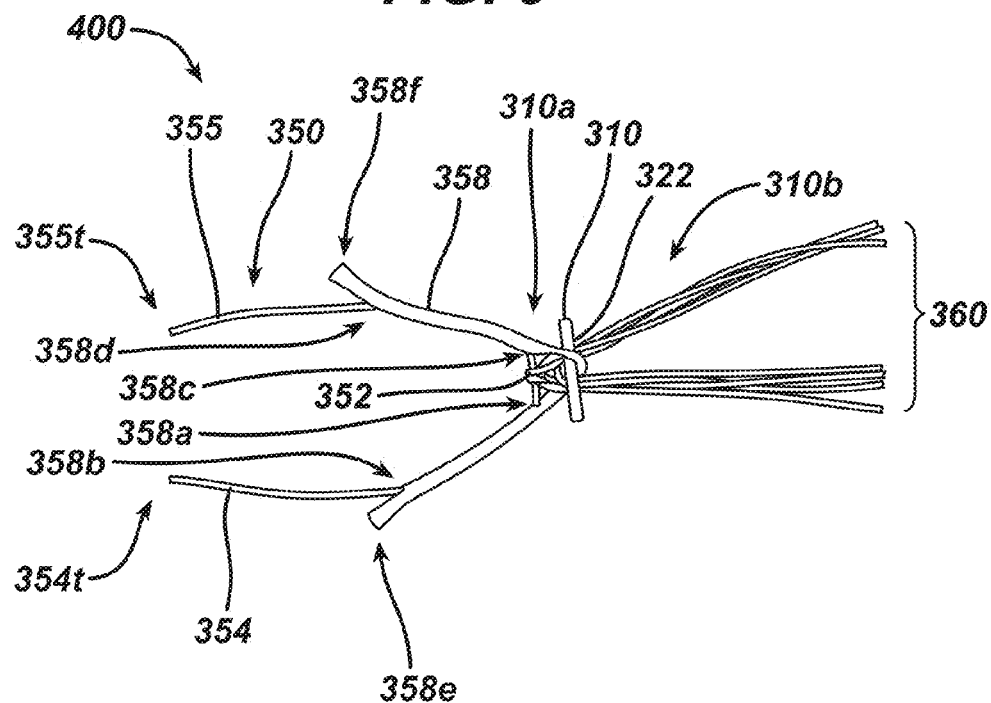
FIG. 9 is a side perspective view of another exemplary embodiment of a surgical implant.

As shown in FIG. 9, in one exemplary embodiment of an implant 400 formed by a body 310 and a suture filament 350 forming both a self-locking knot 352 on a top side 310a of the body 310 and a plurality of coils 360 substantially disposed on a bottom side 310b of the body 310, sleeve 358 is a single suture filament having a plurality of bores formed therein to thread first and second limbs 354, 355 through the sleeve 358. The sleeve 358 can be disposed around a portion of the first limb 354 on the top side 310a, wrap around a bottom surface 322 of the body 310, and then wrap back around to the top side 310a so it can be disposed around a portion of the second limb 355. Wrapping the sleeve 358 around the bottom surface 322 can help minimize proximal movement of the sleeve 358, toward the terminal ends 354t, 355t when the limbs 354, 355 are tightened. The first terminal end 354t passes into the sleeve 358 at a first bore 358a and out of the sleeve at a second bore 358b, while the second terminal end 355t passes into the sleeve 358 at a third bore 358c and out of the sleeve at a fourth bore 358d. As shown, free ends 358e, 358f of the sleeve 358 can extend proximally from the second and fourth bores 358b, 358d.

In other embodiments, the free ends 358e, 358f can be eliminated, or the sleeve can be configured such that the free ends extend distally. The implant 100 of FIG. 1B is an example of an embodiment that does not include free ends. Rather, the first and second terminal ends pass into/out of the sleeve 58 at terminal ends $58t_1$, $58t_2$ of the sleeve rather than at first and fourth bores. In still other embodiments, separate sleeves can be disposed on each of the first and second limbs. In such embodiments, the only bores formed in the sleeves may be those formed at the respective terminal ends, and thus the first and second terminal ends of the filament can pass into and out of the sleeves through the terminal ends of the sleeves. In still further embodiments, the first and second terminal ends can extend through the same sleeve, or alternatively, free ends of the sleeve can be connected together to form a continuous loop. In addition to or in lieu of other sleeve configurations, other components configured to assist in allowing a surgeon to know where to cut the terminal ends after they are no longer needed can also be incorporated into the implants described herein without departing from the spirit of the disclosure.

The sleeve can be made from a wide variety of biocompatible flexible materials, including a flexible polymer, or it can be another filament. In one embodiment the sleeve is made of a polymeric material. In another embodiment, the sleeve is a flexible filament, such as a braided suture, for example Ethibond™ #5 filament. If the sleeve is formed from a high-strength suture such as Orthocord™ #2 filament, the braid can be relaxed by reducing the pick density. For example, Orthocord™ #2 filament, which is typically braided at sixty picks per 2.54 centimeters can be braided at approximately thirty to forty picks per 2.54 centimeters, more preferably at about 36 picks per 2.54 centimeters. If the sleeve material is formed about a core, preferably that core is removed to facilitate insertion of the filament limbs, which may themselves be formed of typical suture such as Orthocord™ #0 suture or #2 suture braided at sixty picks per 2.54 centimeters.

A length and diameter of the sleeve can depend, at least in part, on the size and configuration of the components of the construct with which it is used and the surgical procedure in which it is used. In embodiments in which the sleeve is a filament, a size of the sleeve can be in the range of about a #7 filament (about 18 gauge) to about a #2-0 filament (about 28 gauge), and in one embodiment the size can be about a #5 filament (about 20 gauge to about 21 gauge). In addition, the sleeve can be thickened by folding it upon itself coaxially, (i.e., sleeve in a sleeve). A person having skill in the art will recognize comparable diameters that can be used in instances in which the sleeve is made of a polymeric or other non-filament material. In embodiments in which a single sleeve is disposed over portions of both the first and second terminal ends, a length of the sleeve can be in the range of about 1 centimeter to about 12 centimeters, and in one embodiment the length can be about 5.5 centimeters. In embodiments in which separate sleeves are disposed over portions of the first and second terminal ends, a length of each sleeve can be in the range of about 0.5 centimeters to about 6 centimeters, and in one embodiment each has a length of about 2.5 centimeters. The axially compressible nature of the sleeves can be such that a length of the portion of the sleeve disposed on one of the limbs can compress fully to a length that is in the range of about one-half to about one-eighth the original length of that portion of the sleeve, and in one exemplary embodiment it can compress to a length that is about one-fifth the original length of that portion of the sleeve. Thus, if the length of the sleeve disposed around the first limb is approximately 3 centimeters, when fully compressed the sleeve can have a length that is approximately 0.6 centimeters.

Figure 10:
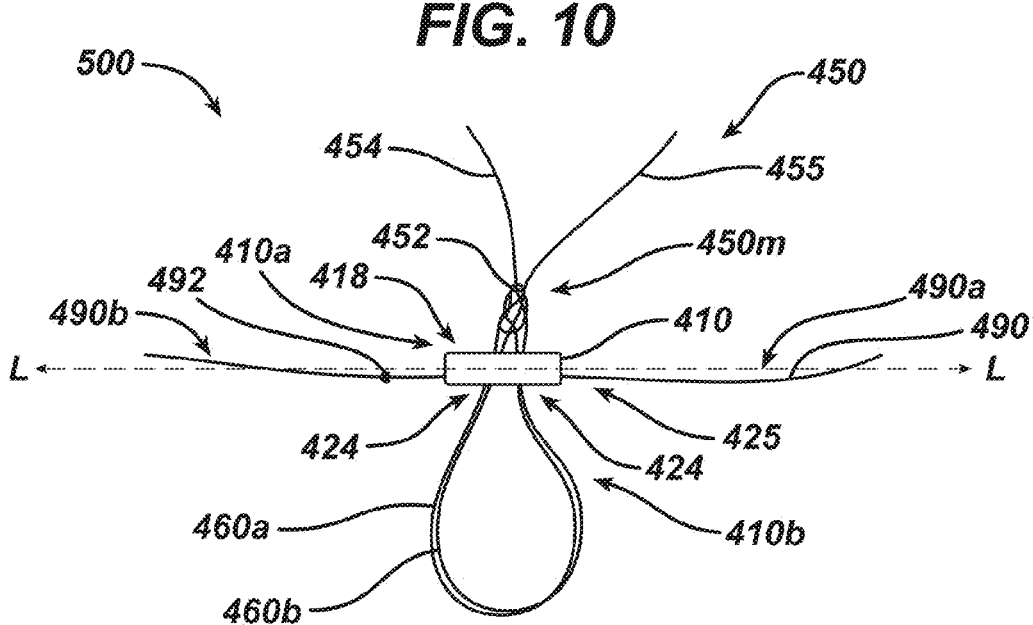
FIG. 10 is a side perspective view of one exemplary embodiment of a surgical implant associated with a shuttle filament.

In some embodiments, a second suture filament can be associated with the body of the implant to help guide or shuttle the filament during a surgical procedure. As shown in FIG. 10, an embodiment of an implant 500 includes a body 410 having two thru-holes 424 formed therein and a first surgical filament 450 coupled thereto. In the illustrated embodiment, rather than having a knot formed on a top side 410a of the body 410, limbs 454, 455 of the first surgical filament 450 are intertwined around a mid-portion 450m of the filament 450 on the top side 410a, thereby forming an intertwining configuration 452. The first and second limbs 454, 455 can also extend distally from the intertwining configuration 452. More particularly, the limbs 454, 455 can extend through the thru-holes 424 a plurality of times to form a plurality of coils 460a, 460b substantially disposed on a bottom side 410b of the body 410. The friction resulting from the intertwining configuration 452 can be sufficient to assist in retaining sizes and positions of the coils 460a, 460b, and to minimize any slipping associated therewith.

A second suture filament or shuttle filament 490 can be disposed longitudinally through the body as shown, for instance in a longitudinal bore 425 formed therethrough. The filament can extend substantially along a central, longitudinal axis L of the body 410, and thus can extend through the thru-holes 424 formed in the body 410, resulting in a leading end 490a and a trailing end 490b. A knot 492 or other protrusion larger than a diameter of the longitudinal bore 425 can be formed in or otherwise located on the trailing end 490b and can assist the leading end 490a and the trailing end 490b in serving as a guide or shuttle for the implant 500, as described in greater detail below with respect to FIGS. 13A-13H. By using a single suture disposed through the longitudinal bore 425 to serve as a shuttle, the number of sutures used in the system can be reduced, thereby simplifying the procedure without diminishing the tactile feedback available to the surgeon once the body 410 has flipped on the femoral cortex.

Although the illustrated bore 425 extends through the body 410 and through each of the thru-holes 424, a person skilled in the art will recognize other configurations that can be formed without departing from the spirit of the present disclosure, such as having the thru-holes 424 situated off-center of the body 410 so they are not intersected by the bore 425, or the bore 425 having a path that does not necessarily extend through each thru-hole 424 or all the way through the body 424. Additionally, in some embodiments the longitudinal bore 425 can be formed with an invagination (not shown) on a trailing end 418 of the body 410 such that it has a diameter that is approximately larger than the diameter of the bore 425 and approximately smaller than the diameter of the knot 492. As a result, the knot 492 can be partially fit inside the body 410 and remain engaged with the body 410 even after the body has been flipped onto the femoral cortex. Once the body 410 is rotated through a specific angle, the knot 492 can disengage with the invagination and the filament 490 can easily be removed from the patient. A person having skill in the art will recognize that the size and depth of the invagination can control, at least in part, the release angle.

A person skilled in the art will recognize that one or more additional filaments, like the second filament 490, can be associated with a variety of implant configurations, including configurations described herein or derivable therefrom. Two further non-limiting examples of implants having second suture filaments for shuttling are illustrated in FIGS. 11A and 11B and 12A and 12B.

Figure 11A:
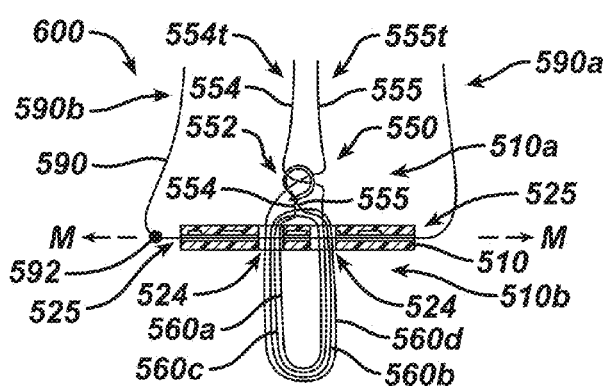
FIG. 11A is a schematic side cross-sectional view of another exemplary embodiment of a surgical implant associated with a shuttle filament.
Figure 11B:
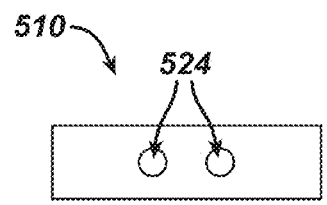
FIG. 11B is a top view of a body of the surgical implant of FIG. 11A.

The implant 600 of FIGS. 11A and 11B includes a body 510 having two thru-holes 524 formed therein and a first surgical filament 550 coupled thereto. The surgical filament 550 is similar to the surgical filament 50 of FIG. 5 in that limbs 554, 555 of the filament 550 are used to form a self-locking knot 552 disposed on a top side 510a of the body 510 and four coils 560a, 560b, 560c, and 560d that pass through the thru-holes 524 and are substantially disposed on a bottom side 510b of the body 510. First and second terminal ends 554t, 555t of the limbs 554, 555 can extend proximally from the self-locking knot 552 and can be used at least to adjust sizes of the coils 560a, 560b, 560c, and 560d in manners consistent with descriptions contained herein. A second suture filament or shuttle filament 590 can be disposed longitudinally through a longitudinal bore 525 formed in the body 510 along a central, longitudinal axis M, and thus can extend through the thru-holes 524 formed in the body 510. Similar to the implant 500 of FIG. 10, a knot 592 larger than a diameter of the longitudinal bore 525 can be formed in a trailing end 590b of the second filament 590 and can assist a leading end 590a and the trailing end 590b in serving as a guide or shuttle for the implant 600.

Figure 12A:
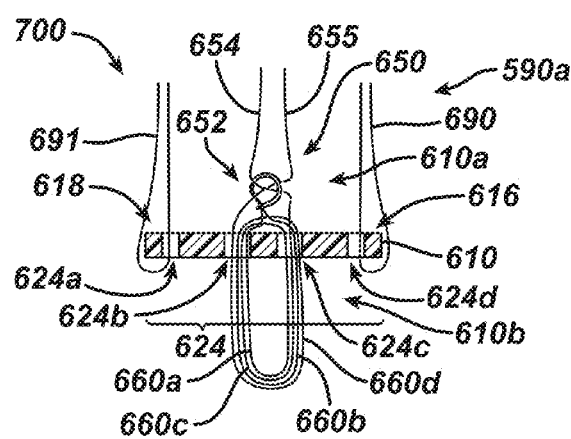
FIG. 12A is a schematic side cross-sectional view of still another exemplary embodiment of a surgical implant associated with a shuttle filament.
Figure 12B:
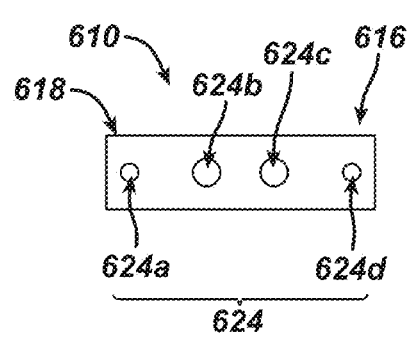
FIG. 12B is a top view of a body of the surgical implant of FIG. 12A.

The implant 700 of FIGS. 12A and 12B includes a body 610 having four thru-holes 624 formed therein and a first surgical filament 650 coupled thereto. As shown, the four thru-holes 624 include two inner thru-holes 624b and 624c that can be used to receive the filament 650 and two outer thru-holes 624a and 624d that can be used to receive shuttle filaments. As shown, the outer thru-holes 624a, 624d can be disposed closer to leading and trailing ends 616 and 618, respectively, than to the inner thru-holes 624b and 624c, and thus the four thru-holes 624 are not approximately equally spaced apart with respect to each other. As also shown, diameters of the two inner holes 624b and 624c are larger than diameters of the two outer holes 624a and 624d. The surgical filament 650 is similar to the surgical filament 50 of FIG. 5 in that first and second limbs 654, 655 of the filament 650 are used to form a self-locking knot 652 disposed on a top side 610a of the body 610 and four coils 660a, 660b, 660c, and 660d that pass through the thru-holes 624b, 624c and are substantially disposed on a bottom side 610b of the body 610. First and second terminal ends 654t, 655t of the limbs 654, 655 can extend proximally from the self-locking knot 652 and can be used at least to adjust sizes of the coils 660a, 660b, 660c, and 660d in manners consistent with descriptions contained herein. As shown, a second, leading suture filament or leading shuttle filament 690 can be disposed through the outer thru-hole 624d and around the leading end 616, and a third, trailing shuttle filament 691 can be disposed through the outer thru-hole 624a and around the trailing end 618. As described below with respect to aspects of FIGS. 13A-13H, the shuttle filaments 690 and 691 can serve as a guide or shuttle for the implant 700 to assist in passing the implant 700 through a bone tunnel.

Similar to other filaments of the present disclosure, a shuttle filament can be an elongate filament of a variety of types, including but not limited to a cannulated filament, a braided filament, and a mono filament. The type, size, and strength of the filament can depend, at least in part, on the other materials of the implant, such as the cortical button, and the type of procedure in which it is used. In one exemplary embodiment the second suture filament is formed from a #5 filament (about 20 gauge to about 21 gauge. In some embodiments the filament can have a size in the range of about a #2-0 filament (about 28 gauge) and about a #5 filament (about 20 gauge to about 21 gauge). A length of the filament can be in the range of about 0.1 meters to about 1.5 meters, and in one embodiment the length is about 1 meter.

Different exemplary features associated with performing an ACL repair using a surgical implant like those described herein are illustrated in FIGS. 13A-13H. The implant 800 illustrated in FIGS. 13A and 13D-G generally includes thru-holes 724 (not shown) formed therein and a first surgical filament 750 coupled thereto. As shown, first and second limbs 754, 755 (FIGS. 13F and 13G) of the first surgical filament 750 can be used to form a self-locking knot 752 disposed on a top side 710a of the body 710 and a plurality of coils—as shown two coils 760a, 760b, but any number of coils can be formed in accordance with the teachings herein—that pass through the thru-holes 724 and are substantially disposed on a bottom side 710b of the body. Extending proximally from the knot can be first and second terminal ends 754t, 755t of the limbs 754, 755, which can be used at least to adjust sizes of the coils 760a, 760b in manners consistent with descriptions contained herein. One or more additional filaments can be associated with the leading and/or trailing ends 716, 718 of the body 710. As shown, a second filament 790 is associated with the leading end 716, and a third filament 791 is associated with the trailing end 716. A graft 802 can be associated with the coils 760a, 760b using techniques known to those skilled in the art.

Figure 13A:
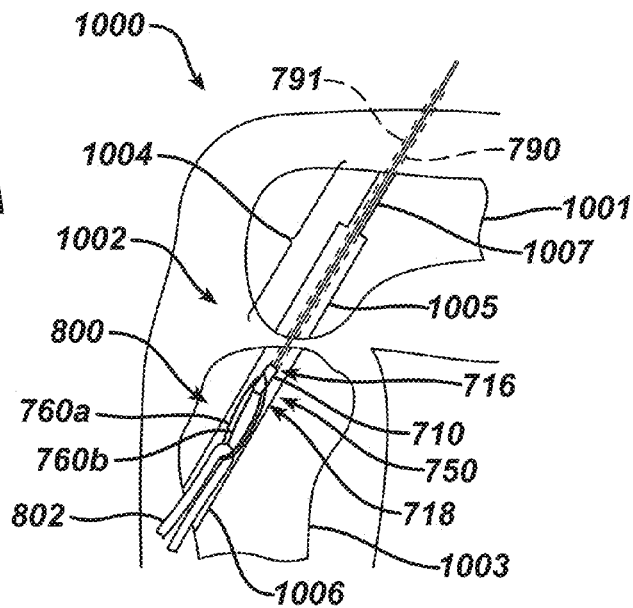
FIG. 13A is a schematic view of a portion of one exemplary embodiment for implanting a graft in a bone tunnel using a surgical implant having a shuttle filament associated therewith.

A surgeon can begin the procedure by preparing the knee 1000 and soft tissue tendon grafts using techniques known by those skilled in the art. As shown in FIG. 13A, a bone tunnel 1002 can be formed in a femur 1001 and tibia 1003, with a femoral tunnel 1004 of the bone tunnel 1002 including a main channel 1005 and a passing channel 1007, the passing channel 1007 having a smaller diameter than the main channel 1005, and the femoral tunnel 1004 being in direct communication with a tibial tunnel 1006 disposed in the tibia 1003. The implant 800 can be introduced into the tibial tunnel 1006 by applying a force in an approximate direction J to the second and third suture filaments 790, 791, which both extend toward the femoral tunnel as shown. The terminal ends 754t, 755t can also extend toward the femoral tunnel, such that six strands of suture all extend out of the femoral tunnel 1004, proximal of the bone tunnel 1002.

Figure 13B:
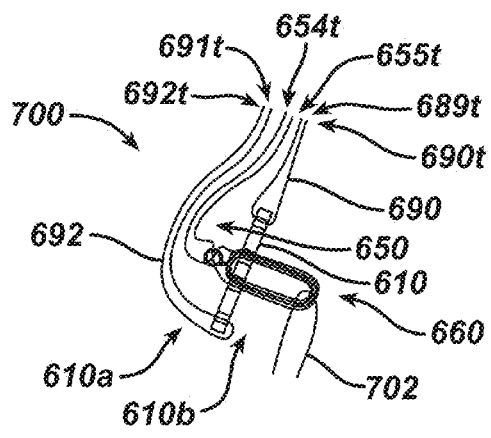
FIG. 13B is a schematic view of the surgical implant of FIG. 12A for use in the exemplary embodiment for implanting a graft in a bone tunnel of FIGS. 13A and 13D-H.
Figure 13C:
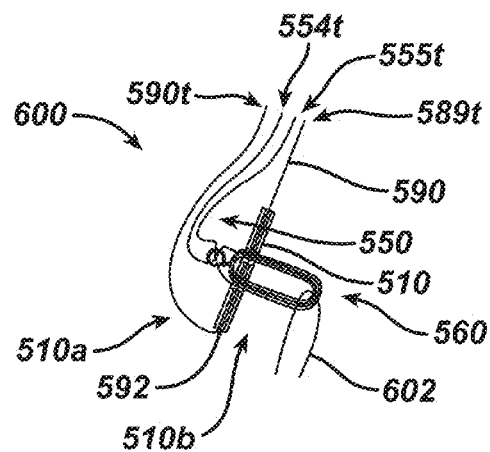
FIG. 13C is a schematic view of the surgical implant of FIG. 11A for use in the exemplary embodiment for implanting a graft in a bone tunnel of FIGS. 13A and 13D-H.

FIGS. 13B and 13C illustrate example orientations for implants 700 and 600 of FIGS. 12A and 12B and FIGS. 11A and 11B, respectively, if they were to be inserted into the bone tunnel 1002 in a manner similar to the implant 800. As illustrated in FIG. 13B, all six terminal ends of the filaments 650, 690, and 691 associated with the body 610 can extend proximally when inserted through the bone tunnel 1002 (not shown). These terminal ends include the first and second terminal ends 654t, 655t of the first filament 650, first and second terminal ends 689t, 690t of the leading shuttle filament 690, and first and second terminal ends 691t, 692t of the trailing shuttle filament 692. Similarly, as illustrated in FIG. 13C, all four terminal ends of the filaments 550 and 590 associated with the body 510 can extend proximally through the bone tunnel 1002 (not shown). These terminal ends include the first and second terminal ends 554t, 555t of the first filament 550 and first and second terminal ends 589t, 590t of the shuttle filament 590. Grafts 702, 602 can be associated with coils 660, 550 of the implants 700, 600 using techniques known to those skilled in the art. Further, a person skilled in the art will recognize that as the implants 700, 600 are inserted into the bone tunnel, filaments and grafts located on the top and bottom sides 610a, 510a and 610b, 510b, respectively, can be flexible to allow the construct to be disposed in the tunnel, similar to the implant 800 of FIG. 13A.

Figure 13D:
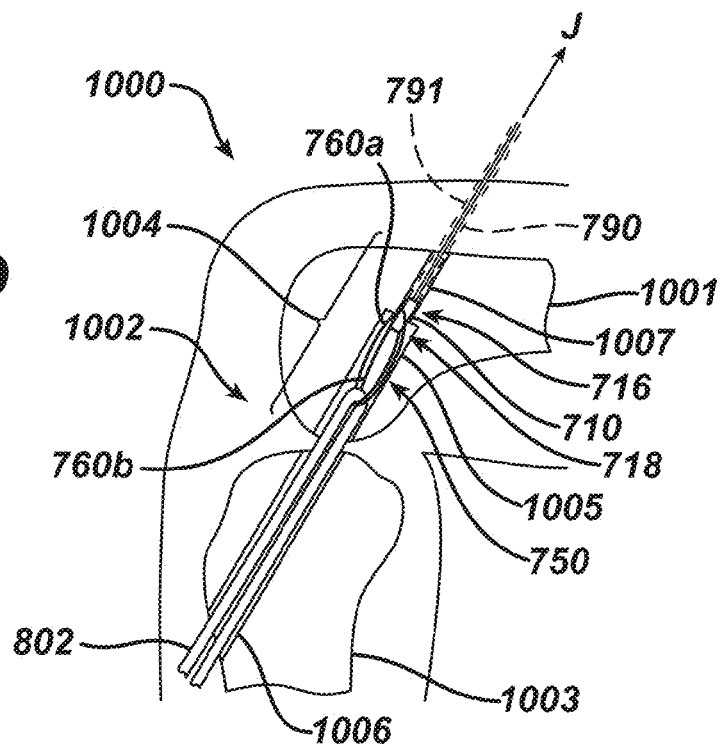
FIGS. 13D-G are schematic, sequential views illustrating the remainder of the exemplary embodiment for implanting a graft in a bone tunnel of FIG. 13A.

Turning back to the implant 800, as shown in FIG. 13D, a force in the approximate direction J can be applied to terminal ends 790t, 791t of the second and third filaments 790, 791, as well as to the terminal ends 754t, 755t of the first and second limbs 754, 755, to advance each through the tibial tunnel 1006 and into the femoral tunnel 1004. A counterforce can be applied to the graft 802 so that the entire construct is not fully inserted into the bone tunnel 1002, as in exemplary embodiments the graft 802 can be used to help orient the cortical button 710 with respect to the bone tunnel 1002. Further, as the body 710 and coils 760a, 760b enter the bone tunnel 1002, care can be taken to prevent the body 710 from becoming wrapped in the coils 760a, 760b. Once the implant 800 enters the bone tunnel 1002, scopes can be used to continue to monitor it. If the coils 760a, 760b undesirably wrap around the body 710, the surgeon can use instruments to unwrap the coils 760a, 760b from the body 710 and/or the surgeon can selectively apply tension to the second and third suture filaments 790, 791 and the graft 802 to manipulate the cortical button 710.

Figure 13E:
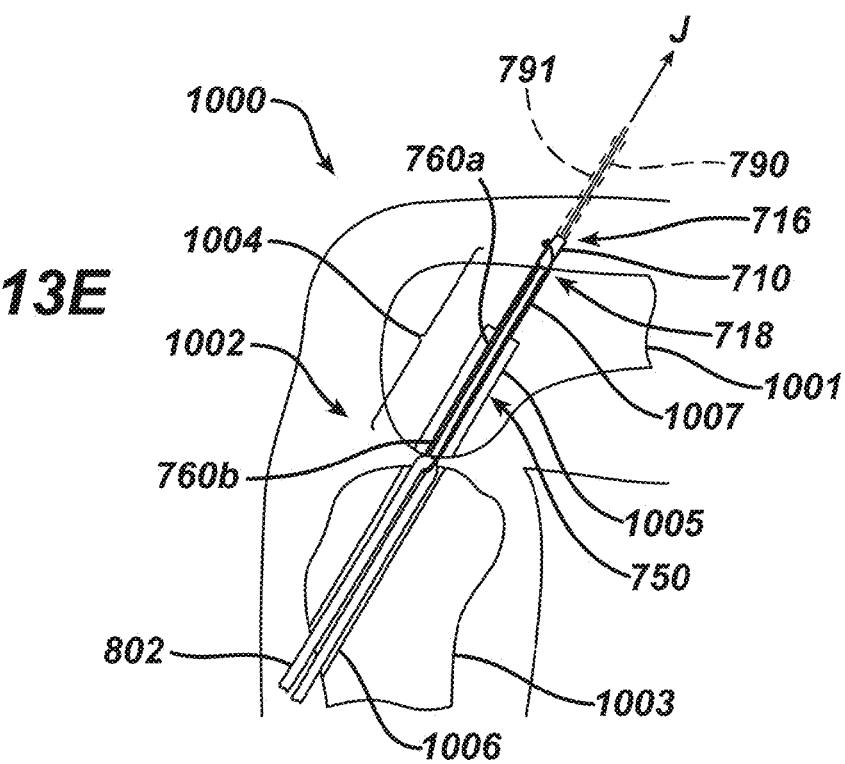
Figure 13F:
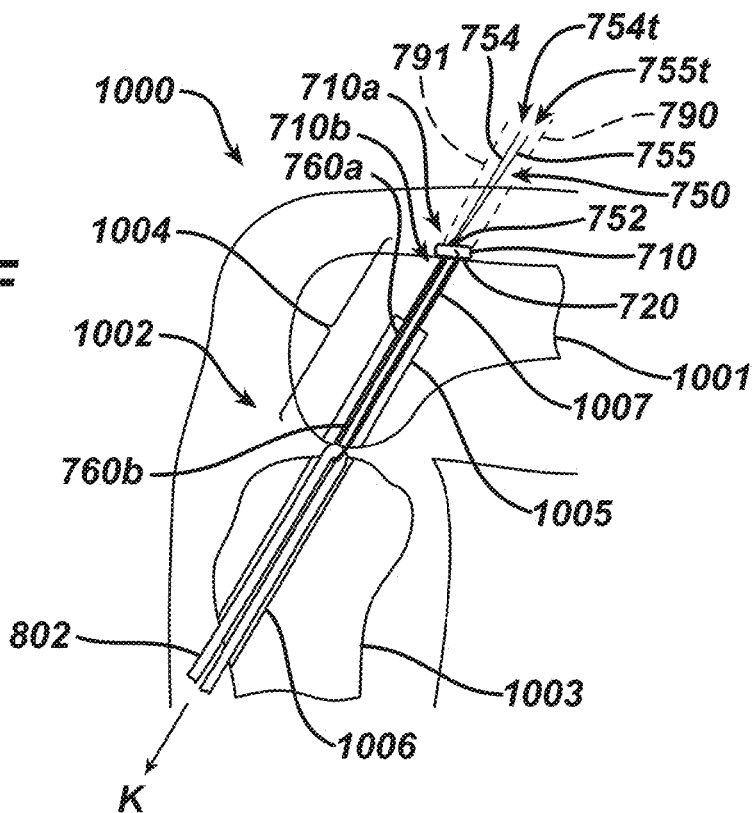
Figure 13G:
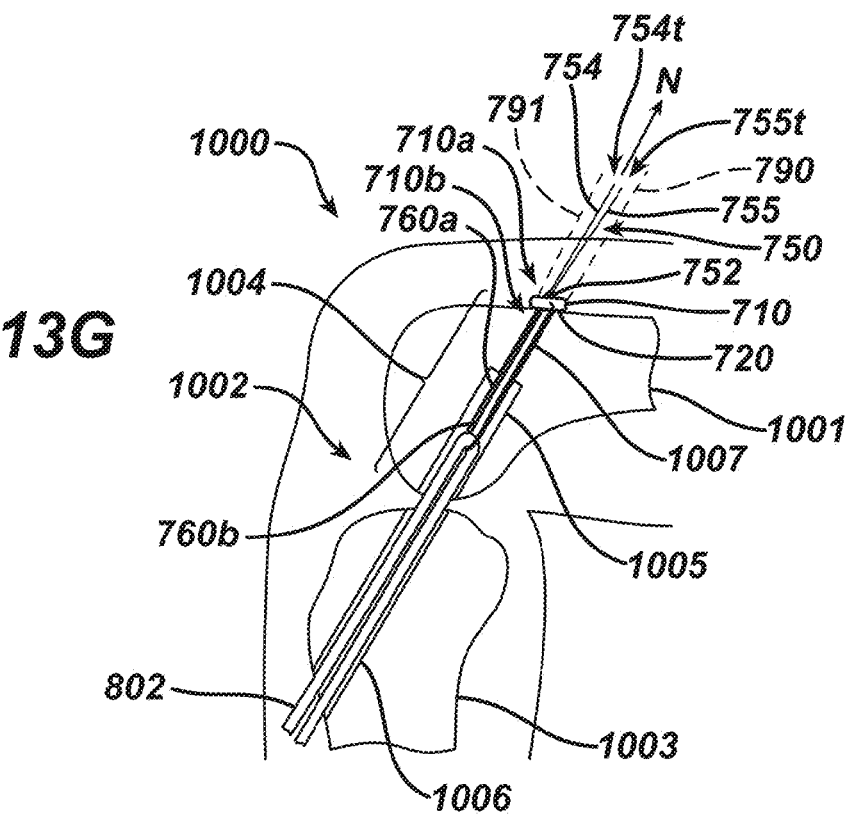

Continued application of the force in the approximate direction J can pull the body 710 through the passing channel 1007. As the body 710 passes through the passing channel 1007 and crests while passing out of the channel, i.e., when a substantial portion of the body is disposed outside of the channel, as shown in FIG. 13E, the surgeon can prepare to orient or manipulate the body so that it flips or changes orientation. Because tissue and ligaments can be located near the proximal end of the femoral tunnel 1004, typically when cortical buttons pass out of a femoral tunnel, the extra tissue can make it difficult to direct the button to a desired location. However, the second and third filaments 790, 791 can assist in manipulating the button 710 to a desired location in which the flat bottom surface 720 rests on the femoral cortex and faces the femoral tunnel 1004, as shown in FIG. 13F. This allows the coils 760a, 760b and graft 802 associated therewith to be disposed in the bone tunnel 1002 and the knot 752 to be located outside of but adjacent to the bone tunnel 1002.

A variety of techniques can be used to flip or reorient the button, but in the illustrated embodiment, shown in FIG. 13F, a force in an approximate direction K is applied to the graft 802, thus tensioning the graft and causing the button 710 to flip. In other embodiments, a surgeon can selectively apply tension to the graft 802 and the second and third filaments 790, 791 to flip the button 710 to its desired location. Once the surgeon has oriented the button 710 as desired, the surgeon can confirm its location as lying flat on the femoral cortex, directly adjacent to the femoral tunnel 1004, using a variety of techniques, including by using tactile feedback received from pulling the second and third filaments 790, 791 and the graft 802, and/or using visual aids.

Once the body 710 is disposed at its desired location, tension can be applied to the terminal ends 754t, 755t of the limbs 754, 755 to adjust the circumference of the coils 760a, 760b, thereby moving the graft 802 within the bone tunnel 1002 to a desired location. The circumferences of the coils 760a, 760b can be adjusted using a number of different techniques, including those described herein. In one exemplary embodiment, illustrated in FIG. 13G, the first and second terminal ends 754t, 755t can be selectively pulled in an approximate direction N to advance the graft 802 through the tunnel 1002.

Figure 13H:
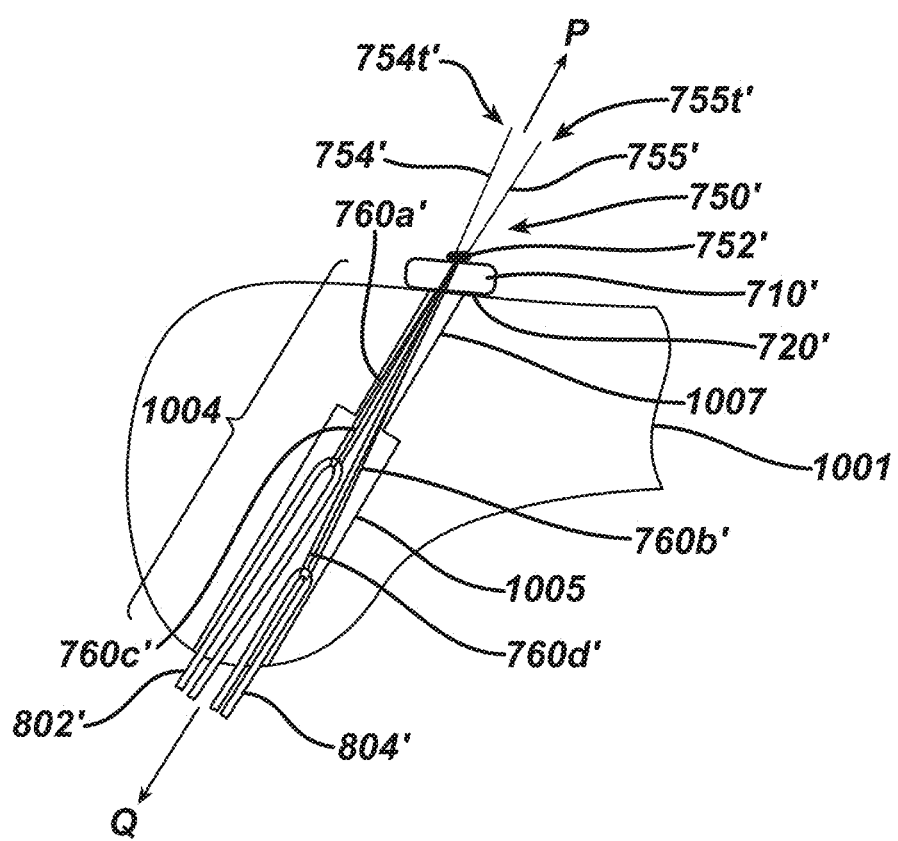
FIG. 13H is a schematic view of a portion of another exemplary embodiment for implanting a graft in a bone tunnel using a surgical implant having two, independently collapsible coils.

Once the implant 800 and graft 802 are positioned in their desired locations, excess filaments can be removed, including portions of the terminal ends 754t, 755t and the second and third filaments 790, 791. In some embodiments the second and third filaments can be completely removed, while care can be taken to ensure that enough material remains with respect to the terminal ends 754t, 755t so as not to negatively impact the integrity of the knot 752. Then the remaining portions of the repair can be carried out, such as steps related to tibial fixation FIG. 13H illustrates an embodiment of an ACL repair method in which a filament 750' is used to form four coils 760a', 760b', 760c', 760d', two (760a', 760c') of which are associated with a first graft 802' and two (760b', 760d') of which are associated with a second graft 804'. As shown in FIG. 13H, the cortical button 710' is already oriented or flipped so that the top surface 720' rests on the femoral cortex and faces the femoral tunnel 1004, for instance relying on techniques disclosed herein, and thus circumferences of the coils 760a', 760b', 760c', 760d' can be adjusted to selectively locate them within the bone tunnel 1002. These techniques include, for instance, those discussed above with respect to FIGS. 6A and 6B. In one exemplary embodiment, tension can be alternately applied in an approximate direction P to first and second terminal ends 754t', 755t' to advance the grafts 802', 804' in increments of approximately 1 centimeter. Alternatively, the grafts 802', 804' can be advanced by using a configuration in which the first and second terminal ends 754t', 755t' are tied together and held in one hand while tension in the approximate direction Q is applied to the grafts 802', 804' by another hand. The surgeon can then alternate between pronation and supination to tighten the filament limbs, and thereby the coils 760a', 760b', 760c', 760d', which in turn advances the grafts 802', 804' proximally through the bone tunnel 1002.

The grafts 802', 804' can be advanced to a desired location, for example up to the passing channel 1007 of the femoral tunnel 1004. When a graft 802', 804' reaches the passing channel 1007, typically the resistance to tightening of the coils 760a', 760b', 760c', 760d' noticeably increases. In some embodiments, such as that illustrated in FIG. 13H, one or more loops 760a', 760c' can have a smaller circumference than other loops 760b', 760d' so that one graft 802' is more proximally located than the other graft 804'. As also illustrated in FIG. 13H, any shuttle filaments used in the method can be removed, and the terminal ends 754t', 755t' can be shortened as described herein.

A person skilled in the art will also recognize how other embodiments described herein or derivable therefrom can be easily adapted for use with the procedures described herein, and in some instances can provide additional benefits. By way of non-limiting example, for embodiments such as those illustrated in FIGS. 11A, 11B, and 13C in which a single filament is used for purposes of shuttling the body, removal of the filament after placement of the cortical button can be easier than if separate filaments are tied to respective leading and trailing ends of the button.

The ability to control two independently tensioned ligament grafts in a single tunnel using a single cortical button is an improvement over existing techniques for ACL repairs. In existing methods for performing ACL repairs, a cortical button having filament associated therewith can only control a single bundle of ligament graft. Thus, if independent movement of multiple ligaments is needed, each ligament is typically associated with its own cortical button. Some surgeons use a double-tunnel technique to implant two ligaments, thus fixing each graft bundle in separate tunnels. Double-tunnel techniques likewise require one button per bundle. Thus, the methods described and resulting from disclosures herein represent improved ACL repair techniques because they allow for two ligament bundles to be independently moved using a single button, and doing so in a single tunnel. This results in procedures that have a reduced risk of complications and is generally less complex than existing procedures. A person skilled in the art will recognize that the disclosures pertaining to independently controlling two filament loops can be broadly applied to a variety of implant designs and surgical procedures, and can even be applied to non-medical fields without departing from the spirit of the present disclosure.

One skilled in the art will appreciate further features and advantages of the invention based on the above-described embodiments. Accordingly, the invention is not to be limited by what has been particularly shown and described, except as indicated by the appended claims. By way of non-limiting example, the exemplary ACL repair methods described herein with respect to FIGS. 13A-13H can be adapted for use with the other implant configurations described herein or derivable from the disclosures herein. All publications and references cited herein are expressly incorporated herein by reference in their entirety.

What is claimed is:

1. A surgical method, comprising:
    loading a graft onto one or more coils of a plurality of coils of an implant filament that is coupled to an implant body, the implant filament forming a sliding knot, and the implant body having a shuttle filament disposed therethrough and two thru-holes each extending separate from the other from a proximal surface of the implant body to a distal surface of the implant body with the plurality of coils being disposed in each of the two thru-holes;
    pulling a leading end of the shuttle filament, and thus the implant body, the implant filament, and the graft, through a bone tunnel until the implant body is pulled out of the tunnel while at least a portion of the implant filament and the graft remain in the tunnel; and
    orienting the implant body so that the distal surface of the implant body is facing the tunnel such that the plurality of coils are disposed substantially within the tunnel and the sliding knot and first and second terminal ends of the implant filament are outside of the tunnel, with the sliding knot being disposed on the proximal surface of the implant body, and the proximal surface of the implant body being opposed to the distal surface of the implant body,
    wherein the plurality of coils comprise a first coil and a second coil formed by a first portion of the implant filament extending between the sliding knot and the first terminal end, and a third coil and a fourth coil formed by a second portion of the implant filament extending between the sliding knot and the second terminal end, and wherein the plurality of coils are each disposed on the distal side of the implant body.

2. The surgical method of claim 1, further comprising:
selectively applying tension to at least one of the first and second terminal ends of the implant filament to adjust a circumference of one or more coils of the plurality of coils.

3. The surgical method of claim 1, wherein the step of orienting the implant body further comprises pulling a trailing end of the shuttle filament.

4. The surgical method of claim 1, wherein the step of orienting the implant body further comprises pulling both the leading end of the shuttle filament and a trailing end of the shuttle filament.

5. The surgical method of claim 4, wherein the step of orienting the implant body by pulling both the leading end of the shuttle filament and the trailing end of the shuttle filament occurs after the implant body is outside the bone tunnel to rotate the implant body such that a bottom surface of the implant body is facing the bone tunnel.

6. The surgical method of claim 1, wherein the implant body includes a second shuttle filament and the step of pulling the leading end of the shuttle filament further includes pulling a leading end of the second shuttle filament.

7. The surgical method of claim 6,
wherein the implant body has a length and a width, the length being greater than the width, and
wherein the second shuttle filament is disposed through the implant body at a second location that is on an opposite end of the length of the body than the location of the shuttle filament.

8. The surgical method of claim 1, wherein the sliding knot is a self-locking knot that includes the first terminal end of the implant filament passed through a collapsible opening of the self-locking knot from a first side of the opening and to a second side of the opening that is opposite the first side of the opening, and the second terminal end of the implant filament passed through the collapsible opening of the self-locking knot from the second side of the opening and to the first side of the opening.

9. The surgical method of claim 1, wherein each of the first, second, third, and fourth coils are disposed in each of the two thru-holes.

10. A surgical method, comprising:
loading a graft onto at least one coil of an implant filament that is coupled to an implant body that includes a plurality of apertures formed therein, the implant body having a shuttle filament disposed therethrough, and the implant filament including a self-locking Lark's Head knot disposed on a side of the implant body that is opposed to a side of the implant body that faces the graft loaded onto the at least one coil; and
pulling a leading end of the shuttle filament to pull the body, the implant filament, and the graft through a bone tunnel until the implant body is pulled out of the tunnel while at least a portion of the implant filament and the graft remain in the tunnel,
wherein the self-locking Lark's Head knot comprises:
a collapsible opening formed by a portion of the implant filament being folded such that a first Limb of the implant filament extends from one side of a fold location at which the implant filament is folded and a second limb of the implant filament extends from an opposite side of the fold location, and the first and second limbs passing adjacent to the fold location such that a size of the collapsible opening changes as the first and second limbs move with, respect to the fold location,
a first terminal end of the first limb passed through the collapsible opening of the self-locking Lark's Head knot from a first side of the opening and to a second side of the opening that is opposite the first side of the opening, and a second terminal end of the second limb passed through the collapsible opening of the self-locking Lark's Head knot from the second side of the opening and to the first side of the opening, wherein each of the first terminal end of the first limb and the second terminal end of the second limb is passed through two of the plurality of apertures prior to passing the first and second terminal ends through the collapsible opening.

11. The surgical method of claim 10, further comprising:
orienting the implant body so that a bottom side of the implant body is facing the tunnel such that the at least one coil is disposed substantially within the tunnel, and the self-locking Lark's Head knot and first and second terminal ends of the implant filament are outside of the tunnel.

12. The surgical method of claim 11, wherein the step of orienting the implant body further comprises pulling a trailing end of the shuttle filament.

13. The surgical method of claim 11, wherein the step of orienting the implant body further comprises pulling both the leading end of the shuttle filament and a trailing end of the shuttle filament.

14. The surgical method of claim 10, wherein the implant body includes a second shuttle filament and the step of pulling the leading end of the shuttle filament further includes pulling a leading end of the second shuttle filament.

15. The surgical method of claim 14,
wherein the implant body has a length and a width, the length being greater than the width, and
wherein the second shuttle filament is disposed through the implant body at a second location that is on an opposite end of the length of the body than the location of the shuttle filament.

16. The surgical method of claim 10, wherein the at least one coil comprises a first coil and a second coil formed by a first portion of the implant filament extending between the self-locking Lark's Head knot and the first terminal end, and a third coil and a fourth coil formed by a second portion of the suture filament extending between the self-locking Lark's Head knot and the second terminal end.

17. The surgical method of claim 10, further comprising:
selectively applying tension to at least one of the first terminal end and the second terminal end of the implant filament to adjust a circumference of one or more coils of the plurality of coils.

18. A surgical method, comprising:
loading a graft onto one or more coils of a plurality of coils of an implant filament that is coupled to an implant body that includes a plurality of apertures formed therein, the implant filament forming a sliding Lark's Head knot, the implant body having a length and a width, the length being greater than the width, a leading end of the implant body at one end of the length, and a trailing end of the implant body is at the other end of the length, the implant body having a leading filament disposed through the leading end of the implant body and a trailing filament disposed through the trailing end of the implant body;

pulling the leading filament and the trailing filament, and thus the implant body, the implant filament, and the graft, through a bone tunnel until the implant body is pulled out of the tunnel while at least a portion of the implant filament and the graft remain in the tunnel; and applying tension to each of the leading filament, the trailing filament, and the graft to orient the implant body so that a bottom side of the implant body is facing the tunnel such that the plurality of coils are disposed substantially within the tunnel and the sliding Lark's Head knot and first and second terminal ends of the implant body are outside of the tunnel, adjacent to a top side of the implant body, wherein the sliding Lark's Head knot comprises:

a collapsible opening formed by a portion of the implant filament being folded such that a first limb of the implant filament extends from one side of a fold location at which the implant filament is folded and a second limb of the implant filament extends from an opposite side of the fold location, and the first and second limbs passing adjacent to the fold location such that a size of the collapsible opening changes as the first and second limbs move with respect to the fold location, a first terminal end of the first limb passed through the collapsible opening of the sliding Lark's Head knot from a first side of the opening and to a second side of the opening that is opposite the first side of the opening, and a second terminal end of the second limb passed through the collapsible opening of the sliding Lark's Head knot from the second side of the opening and to the first side of the opening, wherein each of the first terminal end of the first limb and the second terminal end of the second limb is passed through two of the plurality of apertures prior to passing the first and second terminal ends through the collapsible opening.

19. The surgical method of claim 18, further comprising:

selectively applying tension to at least one of first and second terminal ends of the implant filament to adjust a circumference of one or more coils of the plurality of coils.

20. The surgical method of claim 18, wherein the plurality of coils comprise a first coil and a second coil formed by a first portion of the implant filament extending between the sliding Lark's Head knot and the first terminal end, and a third coil and a fourth coil formed by a second portion of the implant filament extending between the sliding Lark's Head knot and the second terminal end, and wherein the plurality of coils are each disposed on the bottom side of the implant body.

* * * * *